(12) United States Patent
Chandrashekar

(10) Patent No.: US 6,248,872 B1
(45) Date of Patent: Jun. 19, 2001

(54) PARASITIC NEMATODE TRANSGLUTAMINASE, NUCLEIC ACID MOLECULES, AND USES THEREOF

(75) Inventor: Ramaswamy Chandrashekar, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 08/781,420

(22) Filed: Dec. 3, 1996

(51) Int. Cl.[7] .................... C07H 21/04; C07H 21/02; C12P 21/06; C12N 9/00
(52) U.S. Cl. .............. 536/23.1; 435/69.1; 435/70.1; 435/71.1; 435/183; 435/320.1; 536/23.5; 536/24.31; 536/24.33; 536/23.2; 536/23.6
(58) Field of Search ................... 536/23.5, 23.1, 536/24.31, 24.33, 23.2, 23.6; 435/69.1, 320.1, 70.1, 71.1, 183

(56) References Cited

U.S. PATENT DOCUMENTS

| | | |
|---|---|---|
| 4,970,297 | 11/1990 | Castelhano et al. ............... 530/331 |
| 5,124,358 | 6/1992 | Kapil et al. ..................... 514/603 |
| 5,514,579 | * 5/1996 | O'Hara et al. . |
| 5,569,603 | * 10/1996 | Tripp et al. . |
| 5,977,306 | * 11/1999 | Grieve et al. . |

FOREIGN PATENT DOCUMENTS

| | | |
|---|---|---|
| 9003433 | * 4/1990 | (WO) . |
| 9824887 | * 6/1998 | (WO) . |

OTHER PUBLICATIONS

Mierendorg et al. Methology in Sinzeprol. 1987, vol. 152, 458–469.*
Chandrashekar et al. Proc. Natl. Acad. Sci. 1998, vol. 95 (2), 531–6.*
Lustigman et al, Antimicrobial Agents & Chemo–Therapy, 39/9: 1913–1919, Sep. 1995.*
Singh et al, Int. J. Biochem. Cell Biol. 27/12:1285–1291, 1995.*
Finken, et al., "Characterization of the Complete Protein Disulfide Isomerase Gene of *Schistosoma mansoni* and Identification of the Tissues of its Expression," 1994, pp. 135–144, *Molecular and Biochemical Parasitology* 640.
Freedman, et al., "Protein Disulphide Isomerase: Building Bridges in Protein Folding," 1994, pp. 331–336, *TIBS* 19.
Lustigman, S., "Molting, Enzymes and New Targets for Chemotherapy of *Onchocerca volvulus*," 1993, pp. 294–297, *Parasitology Today* 9(8).

Lustigman, "Transglutaminase–Catalyzed Reaction is Important for Molting of *Onchocerca volvulus* Third–Stage Larvae," 1995, pp. 1913–1919, *Antimicrobial Agents and Chemotherapy* 39(9).
Mehta, et al., "Identification of a Novel Transglutaminase from the Filarial Parasite *Brugia malayi* and its Role in Growth and Development," 1992, pp. 1–16, *Molecular and Biochemical Parasitology* 53.
Mehta, et al., "Significance of Transglutaminase–Catalyzed Reactions in Growth and Development of Filarial Parasite, *Brugia malayi*," 1990, pp. 1051–1057, *Biochemical and Biophysical Research Communications* 173(3).
Mehta, et al., "Transglutaminase–Catalyzed Incorporation of Host Proteins in *Brugia malayi* Microfilariae," 1996, pp. 105–114, *Molecular and Biochemical Parasitology* 76.
Rao, et al., "*Brugia malayi* and *Acanthocheilonema viteae*: Antifilarial Activity of Transglutaminase Inhibitors In Vitro," 1991, pp. 2219–2224, *Antimicrobial Agents and Chemotherapy* 35(11).
Singh, et al., "Purification and Characterization of a Novel Transglutaminase from Filarial Nematode *Brugia malayi*," 1994, pp. 625–634, *Eur. J. Biochem.* 225.
Singh, et al., "Purification and Partial Characterization of a Transflutaminase from Dog Filarial Parasite, *Dirofilaria immitis*," 1995, pp. 1285–1291, *Int. J. Biochem. Cell Biol.* 27(12).
Wilson, et al., "The *Onchocerca volvulus* Homologue of the Multifunctional Polypeptide Protein Disulfide Isomerase," 1994, pp. 103–117, *Molecular and Biochemical Parasitology* 68.
Bennett et al., 1988, *Nature*, vol. 334, pp. 268–270.
Hempel et al., 1991, *J. of Immunol*, vol. 146, pp. 3713–3720.
Koivunen et al., 1997, *Genomics*, vol. 42, pp. 397–404.

* cited by examiner

Primary Examiner—Niya Minnifield
(74) Attorney, Agent, or Firm—Heska Corporation

(57) ABSTRACT

The present invention relates to parasitic nematode transglutaminase proteins; to parasitic nematode transglutaminase nucleic acid molecules, including those that encode such transglutaminase proteins; to antibodies raised against such transglutaminase proteins; and to compounds that inhibit parasitic nematode transglutaminase activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic nematodes.

10 Claims, No Drawings

PARASITIC NEMATODE TRANSGLUTAMINASE, NUCLEIC ACID MOLECULES, AND USES THEREOF

FIELD OF THE INVENTION

The present invention relates to parasitic nematode transglutaminase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, inhibitors, and combinations thereof, as well as the use of these compositions to protect animals from diseases caused by parasitic nematodes.

BACKGROUND OF THE INVENTION

Parasitic nematode infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant nematode strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic nematode.

An alternative method to prevent parasitic nematode infection includes administering a vaccine against a parasitic nematode. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic nematodes. Although a number of prominent antigens have been identified in several parasitic nematodes, including in Dirofilaria, there is yet to be a commercially available vaccine developed for any parasitic nematode.

The life cycle of parasitic nematodes generally includes development through four molts, the last two molts taking place in the host animal. Molting is a complex process involving a variety of different mechanisms. However, a lack of understanding of the basic biology, metabolism and biochemistry of parasitic nematodes has resulted in the identification of few targets for chemotherapy or vaccines.

As an example of the complexity of parasitic nematodes, the life cycle of *D. immitis*, the nematode that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system of the dog. One method of demonstrating infection in the dog is to detect the circulating microfilariae. If a dog is maintained in an insect-free environment, the life cycle of the parasite cannot progress. However, when microfilariae are ingested by a female mosquito during blood feeding on an infected dog, subsequent development of the microfilariae into larvae occurs in the mosquito. The microfilariae go through two larval stages (L1 and L2) and finally become mature third stage larvae (L3) which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of the adult heartworms can be determined through thoracic examination.

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic nematodeic infections are also widespread, and all require better treatment, including a preventative vaccine program. *O. volvulus*, for example, causes onchocerciasis (also known as river blindness) in humans. Up to 50 million people throughout the world are reported to be infected with *O. volvulus*, with over a million being blinded due to infection.

Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic nematodes. Although a number of prominent antigens have been identified in several parasitic nematodes, including in Dirofilaria and Onchocerca, there is yet to be an effective vaccine developed for any parasitic nematode.

In just the past few years, there has developed an interest in the identification of larval stage-specific enzymes as potential targets for treatment or prevention of nematode diseases. Nematode transglutaminase-catalyzed reactions have recently been identified as possibly important for the growth, development and survival of nematodes, including Acanthocheilonema vitae, Brugia malayi, and Onchocerca volvulus. See, for example, Mehta, 1992, *Mol. Biochem. Parasitol.*, 53, 1–16; Lustigman, 1995, *Antimicrobial Agents and Chemother.*, 39:9, 1913–1919; Lustigman, 1993, *Parasitology Today*, 9:8, 294–297. However, until now, no compounds or methods based on specific known targets in parasitic nematode development have been designed for treating or preventing parasitic nematode disease.

There remains a need to identify an efficacious composition that protects animals against diseases caused by parasitic nematodes and that, preferably, also protects animals from infection by such nematodes.

SUMMARY OF THE INVENTION

The present invention relates to novel products and processes for prevention and treatment of parasitic nematode infection. According to the present invention there are provided parasitic nematode transglutaminase proteins and mimetopes thereof; nematode nucleic acid molecules, including those that encode such proteins; antibodies raised against parasitic nematode transglutaminase proteins (i.e., anti-parasitic nematode transglutaminase antibodies); and other compounds that inhibit parasitic nematode transglutaminase activity (i.e, inhibitory compounds or inhibitors).

The present invention also includes methods to obtain the proteins, mimetopes, nucleic acid molecules, antibodies and inhibitory compounds herein described. Also included in the present invention are therapeutic compositions comprising such proteins, mimetopes, nucleic acid molecules, antibodies, inhibitory compounds, or mixtures thereof, as well as the use of such therapeutic compositions to protect animals from diseases caused by parasitic nematodes.

One embodiment of the present invention is an isolated nucleic acid molecule that hybridizes under stringent hybridization conditions with a parasitic nematode transglutaminase gene. Preferred parasitic nematode transglutaminase genes of the present invention are transglutaminase genes from *Brugia Malayi*, *Dirofilaria immitis*, and *Onchocerca volvulus*. Such nucleic acid molecules are referred to as nematode transglutaminase nucleic acid molecules. A parasitic nematode transglutaminase gene preferably includes at least one of the following nucleic acid sequences: SEQ ID NO:5, SEQ ID NO:7, SEQ ID NO:8, SEQ ID NO:9, SEQ ID NO:10, SEQ ID NO:12, SEQ ID NO:13, SEQ ID NO:14, or a nucleic acid sequence encoding either the nucleic acid molecule herein designated $nOvTG_{542}$., or the nucleic acid molecule herein designated $nBmTG_{542}$.

Another embodiment of the present invention is an isolated nucleic acid molecule that hybridizes under stringent hybridization conditions with a *Dirofilaria immitis* (*D. immitis*) transglutaminase gene; such nucleic acid molecules are referred to as *Dirofilaria immitis* transglutaminase nucleic acid molecules. A *D. immitis* transglutaminase gene preferably includes the following nucleic acid sequences: SEQ ID NO:5, SEQ ID NO:7, SEQ ID NO:8, SEQ ID NO:9, SEQ ID NO:10, SEQ ID NO:12, SEQ ID NO:13, or SEQ ID NO:14.

The present invention also relates to recombinant molecules, recombinant viruses and recombinant cells that include a transglutaminase nucleic acid molecule of the present invention. Also included are methods to produce such nucleic acid molecules, recombinant molecules, recombinant viruses and recombinant cells.

Another embodiment of the present invention includes a *Dirofilaria immitis* transglutaminase protein, or a protein that includes a *Dirofilaria immitis* transglutaminase protein. A preferred *Dirofilaria immitis* transglutaminase protein is capable of eliciting an immune response when administered to an animal and/or of having parasitic nematode transglutaminase activity. A preferred *Dirofilaria immitis* transglutaminase protein is encoded by a nucleic acid molecule that hybridizes under stringent conditions with a nucleic acid molecule including either SEQ ID NO:7, SEQ ID NO:9, SEQ ID NO:12, or SEQ ID NO:14. A preferred *Dirofilaria immitis* transglutaminase protein includes at least a portion of a protein represented by SEQ ID NO:2, SEQ ID NO:3, SEQ ID NO:4, SEQ ID NO:6 or SEQ ID NO:11.

The present invention also relates to mimetopes of parasitic nematode transglutaminase proteins as well as to isolated antibodies that selectively bind to parasitic nematode transglutaminase proteins or mimetopes thereof. Also included are methods, including recombinant methods, to produce proteins, mimetopes and antibodies of the present invention.

Another embodiment of the present invention is a method to identify a compound capable of inhibiting nematode transglutaminase activity. The method includes the steps of: (a) contacting an isolated nematode transglutaminase protein with a putative inhibitory compound under conditions in which, in the absence of the compound, the protein has nematode transglutaminase activity; and (b) determining if the putative inhibitory compound inhibits the nematode transglutaminase activity. Also included in the present invention is a test kit to identify a compound capable of inhibiting nematode transglutaminase activity. Such a test kit includes an isolated nematode transglutaminase protein having nematode transglutaminase activity and a means for determining the extent of inhibition of the nematode transglutaminase activity in the presence of a putative inhibitory compound.

The present invention also includes an inhibitor of nematode transglutaminase activity identified by its ability to inhibit the activity of a nematode transglutaminase and by its inability to substantially inhibit mammalian transglutaminase. Examples of such inhibitors are substrate analogs of nematode transglutaminase, active site inhibitors of nematode transglutaminase, and antibodies that specifically recognize nematode transglutaminase.

Yet another embodiment of the present invention is a therapeutic composition that is capable of protecting an animal from disease caused by a parasitic nematode. Such a therapeutic composition includes an excipient and one or more of the following protective compounds: an isolated nematode transglutaminase protein or a mimetope thereof; an isolated nucleic acid molecule that hybridizes under stringent hybridization conditions with a nematode transglutaminase gene; an isolated antibody that selectively binds to a nematode transglutaminase protein; an inhibitor of nematode transglutaminase protein activity identified by its ability to (a) inhibit nematode transglutaminase activity, and (b) not substantially inhibit mammalian transglutaminase activity; or any combinations thereof. A preferred therapeutic composition of the present invention also includes an adjuvant, a carrier, or both. Preferred nematode transglutaminase nucleic acid molecule compounds of the present invention include naked nucleic acid vaccines, recombinant virus vaccines and recombinant cell vaccines. Also included in the present invention is a method to protect an animal from disease caused by a parasitic nematode comprising the step of administering to the animal at least one protective compound of the present invention.

Yet another embodiment of the present invention is a method to produce a transglutaminase protein, the method comprising culturing a cell transformed with a nucleic acid molecule that hybridizes under stringent hybridization conditions with a nematode transglutaminase gene.

DETAILED DESCRIPTION OF THE INVENTION

The present invention provides for isolated parasitic nematode transglutaminase proteins, isolated parasitic nematode transglutaminase nucleic acid molecules, antibodies directed against parasitic nematode transglutaminase proteins, and other inhibitors of nematode transglutaminase activity. As used herein, the terms isolated parasitic nematode transglutaminase proteins and isolated parasitic nematode transglutaminase nucleic acid molecules refer to nematode transglutaminase proteins and nematode transglutaminase nucleic acid molecules derived from parasitic nematodes. The proteins and nucleic acid molecules of the present invention can be obtained from their natural source, or they can be produced using, for example, recombinant nucleic acid technology (also referred to herein as recombinant DNA technology) or chemical synthesis. The term non-native parasitic nematode transglutaminase protein, as used herein, refers to a parasitic nematode transglutaminase protein which is produced either synthetically or by transcribing a molecularly cloned or chemically synthesized parasitic nematode transglutaminase nucleic acid molecule of the present invention (in other words, by recombinant DNA technology). Also included in the present invention is the use of these proteins, nucleic acid molecules, antibodies and other inhibitors as therapeutic compositions to protect animals from parasitic nematode diseases as well as in other applications, such as those disclosed below.

Parasitic nematode transglutaminase proteins and nucleic acid molecules of the present invention have utility because they represent novel targets for anti-parasite vaccines and drugs. The products and processes of the present invention are advantageous because they enable the inhibition of crucial steps in nematode molting that involve nematode transglutaminase. While not being bound by theory, it is believed that nematode transglutaminase protein activity is essential for successful development of nematode larvae.

One embodiment of the present invention is an isolated protein comprising a *Dirofilaria immitis* transglutaminase protein. It is to be noted that the term "a" or "an" entity refers to one or more of that entity; for example, a protein refers to one or more proteins or at least one protein. The terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

According to the present invention, an isolated, or biologically pure, protein, is a protein that has been removed from its natural milieu. Accordingly, "isolated" and "biologically pure" do not necessarily reflect the extent to which the protein has been purified. An isolated protein of the present invention can be obtained from its natural source, can be produced using recombinant DNA technology or can be produced by chemical synthesis. When an isolated protein of the present invention is produced using recombinant DNA technology or produced by chemical synthesis, the protein is referred to herein as either an isolated protein or as a non-native protein.

As used herein, an isolated parasitic nematode transglutaminase protein can be a full-length protein or any homolog of such a protein. An isolated protein of the present invention, including a homolog, can be identified in a straightforward manner by the protein's ability to elicit an immune response against parasitic nematode transglutaminase proteins, to exhibit transglutaminase activity, or any combination of these characteristics. Examples of parasitic nematode transglutaminase homologs include parasitic nematode transglutaminase proteins in which amino acids have been deleted (e.g., a truncated version of the protein, such as a peptide), inserted, inverted, substituted, derivatized (e.g., by glycosylation, phosphorylation, acetylation, myristoylation, prenylation, palmitoylation, amidation, addition of glycerophosphatidyl inositol), or any combination of the above, so that the homolog includes at least one epitope capable of eliciting an immune response against a parasitic nematode transglutaminase protein. In other words, when the homolog is administered to an animal as an immunogen, using techniques known to those skilled in the art, the animal will produce an immune response against at least one epitope of a natural parasitic nematode transglutaminase protein. The ability of a protein to effect an immune response can be measured using techniques known to those skilled in the art. Techniques to measure parasitic nematode transglutaminase activity are also known to those skilled in the art, and are described in the Examples.

Parasitic nematode transglutaminase protein homologs can be the result of natural allelic variation or natural mutation. Nematode transglutaminase protein homologs of the present invention can also be produced using techniques known in the art including, but not limited to, direct modifications to the protein or modifications to the gene encoding the protein using, for example, classic or recombinant DNA techniques to effect random or targeted mutagenesis.

Isolated proteins of the present invention have the further characteristic of being encoded by nucleic acid molecules that hybridize under stringent hybridization conditions to a gene encoding a *D. immitis*, a *B. malayi* or an *O. volvulus* nematode transglutaminase protein (i.e., to a *D. immitis*, a *B. malayi* or an *O. volvulus* nematode transglutaminase gene). As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Standard conditions are disclosed, for example, in Sambrook et al., 1989, *Molecular Cloning: A Laboratory Manual*, Cold Spring Harbor Labs Press. The reference Sambrook et al., ibid., is incorporated by reference herein in its entirety. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

As used herein, a parasitic nematode transglutaminase gene includes all nucleic acid sequences related to a natural parasitic nematode transglutaminase gene including, for example, regulatory regions that control production of the nematode transglutaminase protein encoded by that gene (such as, but not limited to, transcription, translation or post-translation control regions), as well as the coding region itself. A *D. immitis* gene can include $dDiTG_{1472}$; a *B. malayi* gene can include $nBmTG_{542}$, and an *O. volvulus* gene can include $nOvTG_{542}$. In one embodiment, a parasitic nematode transglutaminase gene of the present invention includes the nucleic acid sequence SEQ ID NO:5, SEQ ID NO:8, SEQ ID NO: 10, or SEQ ID NO:13, as well as the complement of SEQ ID NO:5, SEQ ID NO:8, SEQ ID NO:10, or SEQ ID NO:13 (i.e. SEQ ID NO:7, SEQ ID NO:9, SEQ ID NO:12, or SEQ ID NO:14, respectively). The nucleic acid sequence SEQ ID NO:8 represents the deduced sequence of the coding strand of the apparent coding region of a cDNA (complementary DNA) molecule denoted herein as $nDiTG_{705}$, the production of which is disclosed in the Examples. The complement of SEQ ID NO:8 (represented herein by SEQ ID NO:9) refers to the nucleic acid sequence of the strand complementary to the strand having SEQ ID NO:8, the sequence of which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited.

Nucleic acid sequence SEQ ID NO:13 represents the deduced sequence of the coding strand of a cDNA nucleic acid molecule denoted herein as $nDiTG_{1107}$, the production of which is disclosed in the Examples. The complement of SEQ ID NO:13 is represented herein by SEQ ID NO:14.

It should be noted that because nucleic acid and amino acid sequencing technology is not entirely error-free, SEQ ID NO:5, SEQ ID NO:8, SEQ ID NO:10, and SEQ ID NO:13, as well as other nucleic acid and protein sequences presented herein, represent apparent nucleic acid sequences of the nucleic acid molecules encoding a parasitic nematode transglutaminase protein of the present invention, and apparent amino acid sequences of the proteins of the present invention, respectively.

In another embodiment, a nematode transglutaminase gene can be an allelic variant that includes a similar but not identical sequence to SEQ ID NO:5, SEQ ID NO:7, SEQ ID NO:8, SEQ ID NO:9, SEQ ID NO:10, SEQ ID NO:12, SEQ ID NO:13 or SEQ ID NO:14. An allelic variant of a nematode transglutaminase gene including SEQ ID NO:5, SEQ ID NO:7, SEQ ID NO:8, SEQ ID NO:9, SEQ ID NO:10, SEQ ID NO:12, SEQ ID NO:13 or SEQ ID NO:14, is a gene that occurs at essentially the same locus (or loci) in the genome as the gene including SEQ ID NO:5, SEQ ID NO:7, SEQ ID NO:8, SEQ ID NO:9, SEQ ID NO:10, SEQ ID NO:12, SEQ ID NO:13 or SEQ ID NO:14, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic nematode, or among a group of two or more parasitic nematodes, because of the diploid nematode genome.

The minimum size of a nematode transglutaminase protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. The size of the nucleic acid molecule encoding such a protein homolog is dependent on nucleic acid composition and percent homology between the nucleic acid molecule and a complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimum size of nucleic acid molecules that can form stable hybrids under standard hybridization conditions is typically at least about 12 to about 15 nucleotides in length if the nucleic acid molecules are GC-rich, and at least about 15 to about 17 bases in length if they are AT-rich. Therefore, the minimum size of a nucleic acid molecule used to encode a nematode transglutaminase protein homolog of the present invention is from about 12 to about 18 nucleotides in length. Accordingly, the minimum size of a nematode transglutaminase protein homolog of the present invention is from about 4 to about 6 amino acids in length. There is no limit, other than a practical limit, on the maximum size of a nucleic acid molecule of the present invention because nucleic acid molecules of the present invention can include a portion of a gene, an entire gene, multiple genes, or portions thereof. The preferred size of a protein encoded by a nucleic acid molecule of the present invention depends on whether a full-length, fusion, multivalent, or functional portion of a protein is desired.

Suitable parasitic nematodes from which to isolate nematode transglutaminase proteins of the present invention (including isolation of the natural protein or production of the natural or non-native protein by recombinant or synthetic techniques) include filarioid, ancylostomatoid, ascaridoid, diochtophymatoid, dracunculoid, metastrongyloid, oxyuroid, physalopteroid, rhabtitoid, spiruroid, strongyloid, thelazioid, trichinelloid, and trichostrongyloid nematodes. Particularly preferred nematodes are those of the genera Dirofilaria, Onchocerca, Brugia, Acanthocheilonema, Aelurostrongylus, Ancylostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Mansonella, Muellerius, Necator, Nematodirus, Oesophagostomum, Ostertagia, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichostrongylus, Trichuris. Uncinaria, and Wuchereria. Particularly preferred are filarioid nematodes including Dirofilaria, Onchocerca, Brugia, Acanthocheilonema, Dipetalonema, Loa, Mansonella, Parafilaria, Setaria, Stephanofilaria, and Wuchereria, with *D. immitis, B. malayi, O. volvulus* and *T. canis* being even more preferred, and *D. immitis* being particularly preferred.

A preferred parasitic nematode transglutaminase protein of the present invention is a compound that is not substantially toxic to host animals (that is, does not substantially inhibit host animal transglutaminase; the term, "does not substantially inhibit" as used herein can be used interchangeably with the term, "inability to substantially interfere"; a compound that does not substantially inhibit host animal transglutaminase activity is one that, when administered to a host animal, the host animal shows no significant adverse effects attributable to the compound) and which, when administered to an animal in an effective manner, is capable of protecting that animal from disease caused by a parasitic nematode. In accordance with the present invention, the ability of a nematode transglutaminase protein of the present invention to protect an animal from disease by a parasitic nematode refers to the ability of that protein to, for example, treat, ameliorate or prevent disease caused by parasitic nematodes. In particular, the phrase, "protect an animal from disease by a parasitic nematode," refers to reducing the potential for parasitic nematode population expansion in the host animal by inhibiting parasitic nematode molting and subsequent growth. Nematode molting is an essential step in the life cycle and development of all nematodes, and characterizes the progression of the nematode larvae through the development of larval stages to the adult. A host animal, as used herein, is an animal in which a parasitic nematode can live and multiply. In one embodiment, a nematode transglutaminase protein of the present invention can elicit an immune response (including a humoral or cellular immune response, or both) against a parasitic nematode.

Suitable nematodes to target with therapeutic compounds of the present invention include any nematodes that are essentially incapable of molting in a host animal when a nematode transglutaminase protein of the present invention, or inhibitor of such a protein, has been administered to that animal. Accordingly, a nematode to target includes any nematode that produces a protein having one or more epitopes that can be neutralized by either a humoral or a cellular immune response, or both, elicited by a nematode transglutaminase protein of the present invention, or that produces a protein that can be targeted by a compound that otherwise inhibits nematode transglutaminase activity, thereby resulting in the decreased ability of the nematode to cause disease in an animal. Preferred nematodes to target include parasitic nematodes disclosed herein as being useful in the production or isolation of parasitic nematode transglutaminase proteins of the present invention.

The present invention also includes mimetopes of parasitic nematode transglutaminase proteins of the present invention. As used herein, a mimetope of a parasitic nematode transglutaminase protein of the present invention refers to any compound that is able to mimic the activity of such a parasitic nematode transglutaminase protein (e.g., has the ability to elicit an immune response against a parasitic nematode transglutaminase protein of the present invention or ability to inhibit parasitic nematode transglutaminase activity), often because the mimetope has a structure that mimics the parasitic nematode transglutaminase protein. It is to be noted, however, that the mimetope need not have a structure similar to a parasitic nematode transglutaminase protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of parasitic nematode transglutaminase proteins of the present invention. Mimetopes can also be obtained by generating random samples of molecules, such as oligonucleotides, peptides or other organic molecules, and screening such samples by affinity chromatography techniques using the corresponding binding partner, (e.g., an anti-parasitic nematode transglutaminase antibody). A preferred mimetope is a peptidomimetic compound that is structurally and/or functionally similar to a parasitic nematode transglutaminase protein of the present invention, particularly to the active site of the parasitic nematode transglutaminase protein.

One embodiment of a parasitic nematode transglutaminase protein of the present invention is a fusion protein that includes a parasitic nematode transglutaminase protein-containing domain attached to one or more fusion segments. Suitable fusion segments for use with the present invention include, but are not limited to, segments that can: enhance a protein's stability; act as an immunopotentiator to enhance an immune response against a nematode transglutaminase protein; assist in purification of a nematode transglutaminase protein (e.g., by affinity chromatography); or any combination of the above listed functions. A suitable fusion segment can be a domain of any size that has the desired function (e.g., imparts increased stability, imparts increased immunogenicity to a protein, or simplifies purification of a protein). Fusion segments can be joined to amino or carboxyl termini, or both, of the nematode transglutaminase-containing domain of the protein and can be susceptible to cleavage in order to enable straightforward recovery of a nematode transglutaminase protein. Fusion proteins are preferably produced by culturing a recombinant cell transformed with a fusion nucleic acid molecule that encodes a protein including the fusion segment attached to either or both of the carboxyl or amino terminal ends of a nematode transglutaminase-containing domain. Preferred fusion segments include a metal binding domain (e.g., a poly-histidine segment); an immunoglobulin binding domain (e.g., Protein A; Protein G; T. cell; B cell; Fc receptor; or complement protein antibody-binding domains); a sugar binding domain (e.g., a maltose-binding domain); a "tag" domain (e.g., at least a portion of β-galactosidase, a strep tag peptide, other domains that can be purified using compounds that bind to the domain, such as monoclonal antibodies), or any combination of the above listed fusion segments. More preferred fusion segments include metal binding domains, such as a poly-histidine segment; a maltose-binding domain; a strep tag peptide, such as that available from Biometra in Tampa, Fla.; and an S10 peptide.

In another embodiment, a parasitic nematode transglutaminase protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one other infectious agent.

Examples of multivalent protective compounds include, but are not limited to, a parasitic nematode transglutaminase protein of the present invention attached to one or more compounds protective against one or more other infectious agents, particularly an agent that infects humans, cats, dogs, cattle, sheep pigs, goats or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fingi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha); and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as other nematode parasites, including, but not limited to those disclosed herein). In one embodiment, a parasitic nematode transglutaminase protein of the present invention is attached to one or more additional compounds protective against parasitic nematode disease. In another embodiment one or more protective compounds, such as those listed above, can be included in a multivalent vaccine comprising a parasitic nematode transglutaminase protein of the present invention and one or more other protective molecules as separate compounds.

A preferred isolated protein of the present invention is a protein encoded by a nucleic acid molecule that hybridizes under stringent hybridization conditions with nucleic acid molecule $nDiTG_{707}$, $nDiTG_{705}$, $nDiTG_{1472}$, $nDiTG_{1107}$, $nBmTG_{542}$, or $nOvTG_{542}$. A further preferred isolated protein is encoded by a nucleic acid molecule that hybridizes under stringent hybridization conditions with a nucleic acid molecule having nucleic acid sequence SEQ ID NO:7, SEQ ID NO:9, SEQ ID NO:12 or SEQ ID NO:14.

Translation of SEQ ID NO:5 suggests that nucleic acid molecule $nDiTG_{707}$ encodes a partial-length parasitic nematode transglutaminase protein of about 235 amino acids, referred to herein as $PDiTG_{235}$, represented by SEQ ID NO:6, assuming an open reading frame having a first codon spanning from about nucleotide 1 through about nucleotide 3 of SEQ ID NO:5. The coding region encoding $PDiTG_{235}$ is represented by nucleic acid molecule $nDiTG_{705}$, having the nucleic acid sequence represented by SEQ ID NO:8 (the coding strand) and SEQ ID NO:9 (the complementary strand). The deduced amino acid sequence SEQ ID NO:6 suggests a protein having a molecular weight of about 27.2 kilodaltons (kD) and an estimated pI of about 5.07.

The amino acid sequence of $PDiTG_{235}$ includes a thioredoxin family active site from residues about 24 to 30. Thioredoxins participate in various redox reactions through the reversible oxidation of an active center disulfide bond Holmgren, A., 1985 *Annual Review of Biochemistry*, 54, 237–271. A number of eukaryotic proteins contain domains evolutionarily related to thioredoxin.

Translation of SEQ ID NO:10 suggests that nucleic acid molecule $nDiTG_{1472}$ encodes a partial-length parasitic nematode transglutaminase protein of about 368 amino acids, referred to herein as $PDiTG_{368}$, represented by SEQ ID NO:11, assuming an open reading frame having a first codon spanning from about nucleotide 2 through about nucleotide 4 of SEQ ID NO:10, and a putative stop codon spanning from about nucleotide 1105 through nucleotide 1107 of SEQ ID NO:10. The coding region encoding $PDiTG_{368}$ (including a putative stop codon) is represented by nucleic acid molecule $nDiTG_{1107}$, having the nucleic acid sequence represented by SEQ ID NO:13 (the coding strand) and SEQ ID NO:14 (the complementary strand). The deduced amino acid sequence SEQ ID NO:11 suggests a protein having a molecular weight of about 42.6 kD and an estimated pI of about 5.71.

The amino acid sequence of $PDiTG_{368}$ (i.e., SEQ ID NO:11) includes: i) a thioredoxin family active site detected from residues 268 to 274; ii) an endoplasmic reticulum (ER) targeting sequence from residues 365 to 368 (KEEL) (proteins that permanently reside in the lumen of ER seem to be distinguished from newly synthesized secretory proteins by the presence of the C-terminal sequence Lys-Asp-Glu-Leu (KDEL); see, for example, Munro et al., 1987, *Cell* 48,899–907; Pelham, 1990, *Trends in Biochemical Sciences*, 15,483–486; and iii) a tachykinin family signature from residues 186 to 202 (tachykinins are a group of biologically active peptides that excite neurons, evoke behavioral responses, are potent vasodilators, and contract many smooth muscles; see, for example, Maggio, 1988, *Annual Review of Neurosciences*, 11,13–28.

More preferred parasitic nematode transglutaminase proteins of the present invention include proteins comprising amino acid sequences that are at least about 80%, preferably at least about 85%, more preferably at least about 90%, and even more preferably at least about 95% identical to amino acid sequence SEQ ID NO:1, SEQ ID NO:2, SEQ ID NO:3, or SEQ ID NO:4. These sequences are described in the Examples. Even more preferred parasitic nematode transglutaminase proteins of the present invention include proteins comprising amino acid sequences that are at least about 50%, preferably at least about 60%, more preferably at least about 70%, more preferably at least about 80%, more preferably at least about 90%, and even more preferably at least about 95% identical to amino acid sequence SEQ ID NO: 6 or SEQ ID NO:11.

More preferred parasitic nematode transglutaminase proteins of the present invention include proteins encoded by a nucleic acid molecule comprising at least a portion of $nDiTG_{707}$, $nDiTG_{705}$, $nDiTG_{1107}$, $nDiTG_{1472}$, $nBmTG_{542}$, or of $nOvTG_{542}$, or at least a portion of allelic variants of these nucleic acid molecules. In one embodiment, a preferred nematode transglutaminase protein of the present invention is encoded by at least a portion of SEQ ID NO:5, SEQ ID NO:8, SEQ ID NO:10, or SEQ ID NO:13, and has an amino acid sequence that includes at least a portion of SEQ ID NO:6 or SEQ ID NO:11. Also preferred is a protein encoded by an allelic variant of a nucleic acid molecule comprising at least a portion of SEQ ID NO:5, SEQ ID NO:8, SEQ ID NO:10, or SEQ ID NO:13. Particularly preferred proteins of the present invention are those comprising an amino acid sequence selected from consisting of SEQ ID NO: 1, SEQ ID NO: 2, SEQ ID NO: 3, SEQ ID NO: 4, SEQ ID NO: 6, and SEQ ID NO: 11, and proteins encoded by an allelic variant of a nucleic acid molecule encoding any of these amino acid sequences. Also preferred is an isolated *D. immitis* transglutaminase protein. An isolated *D. immitis* transglutaminase protein of the present invention can be either native or can be chemically synthesized or produced in a cell transformed with a nucleic acid molecule encoding a *D. immitis* transglutaminase protein.

Another embodiment of the present invention is an isolated nucleic acid molecule that hybridizes under stringent hybridization conditions with a parasitic nematode transglutaminase gene, and particularly with a *D. immitis*, *B. malayi* or *O. volvulus* transglutaminase gene. The identifying characteristics of such a gene are herein described. A nucleic acid molecule of the present invention can include an isolated natural parasitic nematode transglutaminase gene or a homolog thereof, the latter of which is described in more detail below. A nucleic acid molecule of the present invention can include one or more regulatory regions, full-length or partial coding regions, or any combinations thereof. The minimum size of a nucleic acid molecule of the present invention is the minimum size that can form a stable hybrid with a parasitic nematode transglutaminase gene under stringent hybridization conditions. Suitable and preferred parasitic nematodes are disclosed above.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As used herein, the term, "isolated," does not reflect the extent to which the nucleic acid molecule has been purified. An isolated parasitic nematode transglutaminase nucleic acid molecule of the present invention can be isolated from its natural source or can be produced using recombinant DNA technology (e.g., polymerase chain reaction (PCR) amplification, cloning) or chemical synthesis. Isolated nematode transglutaminase nucleic acid molecules can include, for example, natural allelic variants and nucleic acid molecules modified by nucleotide insertions, deletions, substitutions, inversions, variants created during PCR amplification, or any combination of the above modifications. According to the present invention, acceptable modifications to nematode transglutaminase nucleic acid molecules do not substantially interfere with the nucleic acid molecule's ability to encode a nematode transglutaminase protein of the present invention or to form stable hybrids under stringent conditions with natural parasitic nematode transglutaminase gene isolates.

A parasitic nematode transglutaminase nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments, and PCR amplification), or synthesis of oligonucleotide mixtures and ligation of mixture groups to "build" a mixture of nucleic acid molecules and combinations thereof Nucleic acid molecule homologs can be selected by hybridization with a nematode transglutaminase gene or by screening expression products of the nematode transglutaminase nucleic acid molecule homologs for the function of a protein encoded by the nucleic acid molecule (e.g., the ability to elicit an immune response against at least one epitope of a parasitic nematode transglutaminase protein or parasitic nematode transglutaminase activity).

An isolated nucleic acid molecule of the present invention can include a nucleic acid sequence that encodes at least one parasitic nematode transglutaminase protein of the present invention; examples of such proteins are herein disclosed. Although the phrase "nucleic acid molecule" primarily refers to the physical nucleic acid molecule and the phrase "nucleic acid sequence" primarily refers to the sequence of nucleotides in the nucleic acid molecule, the two phrases can be used interchangeably, especially with respect to a nucleic acid molecule, or a nucleic acid sequence, being capable of encoding a parasitic nematode transglutaminase protein.

A preferred nucleic acid molecule of the present invention, when administered to an animal, is substantially not toxic to the animal and is capable of protecting that animal from disease caused by a parasitic nematode. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., a nematode transglutaminase protein of the present invention), the nucleic acid molecule being delivered to the animal, for example, by direct injection (i.e, as a composition comprising a naked nucleic acid molecule of the present invention) or in a vehicle such as a recombinant virus vaccine or a recombinant cell vaccine.

One embodiment of the present invention is a parasitic nematode transglutaminase nucleic acid molecule that hybridizes under stringent hybridization conditions with nucleic acid molecule nDiTG$_{707}$, and preferably with a nucleic acid molecule having nucleic acid sequence SEQ ID NO:5 or SEQ ID NO:7. Such a nucleic acid molecule would also hybridize with nDiTG$_{705}$, and thus would also hybridize with SEQ ID NO:8 or SEQ ID NO:9. Comparison of nucleic acid sequence SEQ ID NO:5 (i.e., the nucleic acid sequence of the coding strand of nDiTG$_{707}$) with nucleic acid sequences reported in GenBank™ indicates that SEQ ID NO:5 showed the most homology (i.e., about 37% identity) with human clone PA3 (GenBank™ accession number J05016), a protein disulfide isomerase related to protein (Erp72) mRNA.

Another embodiment of the present invention is a parasitic nematode transglutaminase nucleic acid molecule that hybridizes under stringent hybridization conditions with nucleic acid molecule nDiTG$_{1427}$, and preferably with a nucleic acid molecule having nucleic acid sequence SEQ ID NO:10 or SEQ ID NO:12. Such a nucleic acid molecule would also hybridize with nDiTG$_{1107}$, and thus would also hybridize with SEQ ID NO:13 or SEQ ID NO:14. Comparison of nucleic acid sequence SEQ ID NO:10 (i.e., the nucleic acid sequence of the coding strand of nDiTG$_{1427}$) with nucleic acid sequences reported in GenBank™ indicates that SEQ ID NO: 10 showed the most homology (i.e., about 63% sequence identity) with a human epithelial cell mRNA for ER-60 protease (Genank™ accession number D83485), spanning from nucleotide about 1143 to about 1458 of the ER-60 protease.

Preferred parasitic nematode transglutaminase nucleic acid molecules include nucleic acid molecules having a nucleic acid sequence that is at least about 70%, preferably at least about 75%, more preferably at least about 80%, more preferably at least about 85%, even more preferably at least about 90% and even more preferably at least about 95% identical to nucleic acid sequence SEQ ID NO:5, SEQ ID NO:7, SEQ ID NO:8, SEQ ID NO:9, SEQ ID NO:10, SEQ ID NO:12, SEQ ID NO:13, or SEQ ID NO:14.

Another preferred embodiment of the present invention includes at least a portion of a nucleic acid sequence SEQ ID NO:5, SEQ ID NO:7, SEQ ID NO:8, SEQ ID NO:9, SEQ ID NO:10, SEQ ID NO:12, SEQ ID NO:13, or SEQ ID NO:14 that is capable of hybridizing with a *D. immitis* transglutaminase gene of the present invention, as well as allelic variants thereof. Such nucleic acid molecules can include nucleotides in addition to those included in the sequences listed above, such as, but not limited to, a full-length gene, a full-length coding region, a nucleic acid molecule encoding a fusion protein, or a nucleic acid molecule encoding a multivalent protective compound. Particularly preferred nucleic acid molecules include nDiTG$_{707}$, nDiTG$_{705}$, nDiTG$_{1472}$, nDiTG$_{1107}$, nBmTG$_{542}$, and nOvTG$_{542}$, and allelic variants of these nucleic acid molecules. Also particularly preferred nucleic acid molecules include those including SEQ ID NO:5, SEQ ID NO:7, SEQ ID NO:8, SEQ ID NO:9, SEQ ID NO:10, SEQ ID NO:12, SEQ ID NO:13, or SEQ ID NO:14, and allelic variants of these preferred nucleic acid molecules.

The present invention also includes a nucleic acid molecule encoding a protein having at least a portion of SEQ ID NO:6 or SEQ ID NO:11, including allelic variants of these sequences and nucleic acid molecules that have been modified to accommodate codon usage properties of the cells in which such nucleic acid molecules are to be expressed. Particularly preferred are nucleic acid molecules that include SEQ ID NO:1, SEQ ID NO:2, SEQ ID NO:3, SEQ ID NO:4, SEQ ID NO:6 or SEQ ID NO: 11, and allelic variants of these nucleic acid molecules.

Knowing the nucleic acid sequences of certain parasitic nematode transglutaminase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain parasitic nematode transglutaminase nucleic acid molecules from other parasitic nematodes. Such nucleic acid molecules can be obtained in a variety of ways including screening appropriate expression libraries with antibodies of the present invention; traditional cloning techniques using oligonucleotide probes of the present invention to screen appropriate libraries DNA, or RNA; and PCR amplification of appropriate libraries, DNA, or RNA using oligonucleotide primers of the present invention. Preferred libraries to screen or from which to amplify nucleic acid molecule include adult and larval stage parasitic nematode cDNA libraries as well as genomic DNA libraries. Similarly, preferred DNA or RNA sources to screen or from which to amplify nucleic acid molecules include adult and larval stage parasitic nematode cDNA, adult and larval mRNA, and genomic DNA. Techniques to clone and amplify genes are disclosed, for example, in Sambrook et al., ibid, as well as in the Examples section.

The present invention also includes nucleic acid molecules that are oligonucleotides capable of hybridizing, under stringent hybridization conditions, with complementary regions of other, preferably longer, nucleic acid molecules of the present invention such as those comprising parasitic nematode transglutaminase genes or other parasitic nematode transglutaminase nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit nematode transglutaminase protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulation of parasitic nematode transglutaminase nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a cell. As used herein, an expression vector is a DNA or RNA vector that is capable of transforming a cell and of effecting expression of a specified nucleic acid molecule. Preferably, the expression vector is also capable of replicating within the cell. Expression vectors can be either prokaryotic or eukaryotic, and are typically viruses (including viral genomes) or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, insect and mammalian cells, such as, but not limited to, tac, lac, trp, trc, oxy-pro, omp/lpp, rrnB, bacteriophage lambda(such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic nematodes, for example *D. immitis*.

Suitable and preferred nucleic acid molecules to include in recombinant vectors of the present invention are as disclosed herein. Particularly preferred nucleic acid molecules to include in recombinant vectors, and particularly in recombinant molecules, include $nDiTG_{705}$, $nDiTG_{707}$, $nDiTG_{1107}$, $nDiTG_{1472}$, $nBmTG_{542}$, and $nOvTG_{542}$.

Recombinant molecules of the present invention may also (a) contain secretory signals (i.e., signal segment nucleic acid sequences) to enable an expressed nematode transglutaminase protein of the present invention to be secreted from the cell that produces the protein and/or (b) contain fusion sequences that lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention. An example of a preferred intervening sequence for eukaryotic gene expression os cytomegalovirus intron A.

Another embodiment of the present invention includes a recombinant cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. A nucleic acid molecule of the present invention that has been transformed into a cell is referred to herein as a transformed nucleic acid molecule. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include parasitic nematode transglutaminase nucleic acid molecules disclosed herein. Particularly preferred nucleic acid molecules with which to transform a cell include $nDiTG_{705}$ and $nDiTG_{1107}$. Also preferred are $nDiTG_{707}$, $nDiTG_{1472}$, $nBmTG_{542}$, and $nOvTG_{542}$.

Suitable cells to transform include any cell that can be transformed with a nucleic acid molecule of the present invention. A transformed cell of the present invention is also referred to herein as a recombinant cell. Suitable cells can be either untransformed cells or cells that are already transformed with at least one nucleic acid molecule (e.g., nucleic acid molecules encoding one or more proteins of the present invention, other proteins useful in the production of multivalent vaccines, or a combination thereof). Suitable cells for transformation according to the present invention can be either a) endogenously (i.e., naturally) capable of producing parasitic nematode transglutaminase proteins of the present invention, or b) capable of producing such proteins after transformation with at least one nucleic acid molecule of the present invention. Cells of the present invention can be any cell capable of producing at least one protein of the present invention, and include bacterial, fungal (including yeast), insect, other nematode, other and plant cells. Preferred cells for transformation by nucleic acid molecules of the present invention include bacterial, mycobacterial, yeast, parasite, insect and mammalian cells. More preferred cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred cells for transformation are *Escherichia coli*, including *E. coli* K-12 derivatives; *Salmonella typhi; Salmonella typhimurium*, including attenuated strains such as UK-1 $_\chi3987$ and SR-11 $_\chi4072$; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cells suitable for transformation by nucleic acid molecules of the present invention include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a suitable cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a suitable cell as described above.

A recombinant molecule of the present invention is a molecule that can include at least one of any parasitic nematode transglutaminase nucleic acid molecule herein described, operatively linked to at least one of any transcription control sequence capable of effectively regulating expression of the nucleic acid molecule(s) in the cell suitable for transformation, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein.

Recombinant cells of the present invention can also be co-transformed with one or more recombinant molecules including parasitic nematode transglutaminase nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a transformed cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules of the present invention to nucleic acid molecules that direct the production of a high-copy number of plasmids, integration of the nucleic acid molecules into one or more chromosomes in the transformed cell, addition of vector stability sequences to plasmids containing nucleic acid sequences of the present invention, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the transformed cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated nematode transglutaminase proteins of the present invention can be produced in a variety of ways, including production and recovery of natural proteins, production and recovery of recombinant proteins, and chemical synthesis of the proteins. In one embodiment, an isolated parasitic nematode transglutaminase protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a parasitic nematode transglutaminase protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and transformed cell system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, can refer to collecting the whole fermentation medium containing the protein and need not imply additional steps of separation or purification. Proteins of the present invention can be purified using a variety of standard protein purification techniques, such as, but not limited to, affinity chromatography, immunoaffinity chromatography, thermoprecipitation, ammonium sulphate precipitaion, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a parasitic nematode transglutaminase protein of the present invention or a mimetope thereof (e.g., anti-parasitic nematode transglutaminase antibodies). As used herein, the term "selectively binds to" a nematode transglutaminase protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-parasitic nematode transglutaminase antibody preferably selectively binds to a parasitic nematode transglutaminase protein in such a way as to reduce the activity of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein (ranging in size from a peptide to a full length protein) or mimetope thereof of the present invention to produce the antibodies and (b) recovering the antibodies. In another method, antibodies of the present invention are produced recombinantly using techniques as disclosed to produce parasitic nematode transglutaminase proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic nematodes susceptible to treatment by such antibodies, (b) as reagents in assays to detect infection by such nematodes, (c) as tools to screen expression libraries, (d) as tools to recover desired proteins of the present invention from a mixture of proteins and other contaminants, and (e) for any combination of the above listed uses. Furthermore, antibodies of the present invention can be used to target cytotoxic agents to parasitic nematodes of the present invention in order to directly kill such nematodes. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic nematode. Therapeutic compositions of the present invention include an excipient and at least one of the following protective compounds: an isolated native nematode transglutaminase protein; an isolated non-native nematode transglutaminase protein; a mimetope of a nematode transglutaminase protein; an isolated nucleic acid molecule that hybridizes under stringent hybridization conditions with a nematode transglutaminase gene; an isolated antibody that selectively binds to a nematode transglutaminase protein, an inhibitor of nematode transglutaminase protein activity identified by its ability to inhibit nematode transglutaminase activity and its inability to substantially interfere with host animal transglutaminase activity, or a mixture thereof (i.e., combination of at least two of the compounds). The term "inability to substantially interfere with" host animal transglutaminase activity, as used herein, refers to the failure of a nematode transglutaminase inhibitor compound to inhibit host animal transglutaminase activity to such a degree that such an inhibitor is not substantially toxic to a host animal when it is administered to that animal. The inability to interfere with host animal transglutaminase activity can be identified by transglutaminase assay in vitro, as described in the Examples section. Candidate inhibitors can also be tested for toxicity in standard animal studies. Preferred parasitic nematodes to target are herein disclosed.

Examples of proteins, nucleic acid molecules, antibodies and inhibitors of the present invention are disclosed herein.

The present invention also includes a therapeutic composition comprising at least one nematode transglutaminase-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals and birds, and more preferably to dogs, cats, humans, ferrets, horses, cattle, sheep, goats and pigs as well as other pets, food animals, work animals or zoo animals. Preferred animals to protect against parasitic nematode disease include dogs, cats, humans and ferrets, with dogs, cats and humans being particularly preferred.

Suitable inhibitors of nematode transglutaminase activity include compounds that interact directly with a nematode transglutaminase protein active site, thereby inhibiting transglutaminase activity, usually by binding to or otherwise interacting with or otherwise modifying the nematode transglutaminase active site. Nematode transglutaminase inhibitors can also interact with other regions of the nematode transglutaminase protein to inhibit transglutaminase activity, for example, by allosteric interaction. Inhibitors of nematode transglutaminases can be relatively small compounds, or they can be quite large, as in the case of anti-parasitic nematode transglutaminase antibodies. Preferably, a nematode transglutaminase inhibitor of the present invention is identified by its ability to inhibit the activity of a nematode transglutaminase, and further by its failure to substantially inhibit the activity of host animal transglutaminase. Methods for measuring inhibition of transglutaminase activity, useful for determining inhibition of either nematode or host animal transglutaminase activity, are described in the Examples section.

Inhibitors of a nematode transglutaminase can be used directly as compounds in compositions of the present invention to treat host animals, provided that such compounds do not substantially inhibit the activity of the host animal transglutaminase.

Inhibitors of a nematode transglutaminase protein can also be used to identify preferred types of nematode transglutaminase proteins to target using compositions of the present invention, for example by affinity chromatography. For example, an inhibitor of the present invention could be bound to a gel or a filter, or another substrate, and larval or adult nematode extracts could be contacted with the bound inhibitor. Those compounds in either larval or adult nematode extracts that bound to or otherwise interacted with the inhibitor could then be separated from the bound inhibitor and further analyzed for nematode transglutaminase activity.

Preferred inhibitors of a nematode transglutaminase of the present invention include, but are not limited to, nematode transglutaminase substrate analogs and other molecules that bind to a nematode transglutaminase (e.g., to an allosteric site) in such a manner that nematode transglutaminase activity of the nematode transglutaminase is inhibited. A nematode transglutaminase substrate analog refers to a compound that interacts with (e.g., binds to, associates with, modifies) the active site of a nematode transglutaminase protein. A preferred nematode transglutaminase substrate analog inhibits nematode transglutaminase activity. Nematode transglutaminase substrate analogs can be any inorganic or organic composition, and can be, but are not limited to, peptides, nucleic acids, and peptidomimetic compounds.

Nematode transglutaminase substrate analogs can be, but need not be, structurally similar to a nematode transglutaminase protein's natural substrate provided they can interact with the active site of that nematode transglutaminase protein. Nematode transglutaminase substrate analogs can be designed using computer-generated structures of nematode transglutaminase proteins of the present invention or computer structures of nematode transglutaminase proteins' natural substrates. Substrate analogs can also be obtained by generating random samples of molecules (for example, oligonucleotides, peptides, peptidomimetic compounds, or other inorganic or organic molecules), and screening such samples by affinity chromatography techniques using the corresponding binding partner, (e.g., a nematode transglutaminase or anti-nematode transglutaminase substrate antibody). A preferred nematode transglutaminase substrate analog is a peptidomimetic compound (i.e., a compound that is structurally or functionally similar to a natural substrate of a nematode transglutaminase of the present invention, particularly to the region of the substrate that interacts with the nematode transglutaminase active site, but that inhibits nematode transglutaminase activity upon interacting with the nematode transglutaminase active site).

Parasitic nematode transglutaminase peptides, mimetopes and substrate analogs, as well as other protective compounds (nucleic acid molecules, proteins, antibodies, for example), can be used directly as compounds in compositions of the present invention to treat animals as long as such compounds are not harmful to the animals being treated. Methods to test the safety of such compounds are disclosed herein.

In accordance with the present invention, a host animal (i.e., an animal that is infected with or is capable of being infected by a parasitic nematode) is treated by administering to the animal a therapeutic composition of the present invention in such a manner that the composition itself ((e.g., an inhibitor of a nematode transglutaminase protein, mimetope, a nematode transglutaminase synthesis suppressor (i.e., a compound that decreases the production of nematode transglutaminase in the nematode), a nematode transglutaminase mimetope or an anti-parasitic nematode transglutaminase antibody)) or a product generated by the animal in response to administration of the composition (e.g., antibodies produced in response to a parasitic nematode transglutaminase protein or nucleic acid molecule vaccine, or conversion of an inactive inhibitor "prodrug" to an active inhibitor of a nematode transglutaminase protein) contacts the nematode, thereby reducing transglutaminase activity in the nematode. A host animal is preferably treated in such a way that the compound or product thereof enters the bodily fluids (e.g., blood and lymph systems) and/or tissues of the animal. Parasitic nematodes are then exposed to the composition or product when they are present in the host animal. For example, nematode transglutaminase protein inhibitors administered to an animal are administered in such a way that the inhibitors enter the blood and tissues of the animal where parasitic nematodes will come in contact with the inhibitors. In another embodiment, when a parasitic nematode transglutaminase protein, mimetopes or nucleic acid molecule vaccine is administered to a host animal, the treated animal mounts an immune response resulting in the production of antibodies against the parasitic nematode transglutaminase protein (i.e., anti-parasitic nematode transglutaminase antibodies) that circulate in the animal's blood stream and/or other bodily fluids thereby coming into contact with parasitic nematodes.

In order to protect an animal from disease caused by a parasitic nematode of the present invention, a therapeutic composition of the present invention is administered to the animal in an effective manner such that the composition is capable of protecting that animal from a disease caused by a parasitic nematode. Therapeutic compositions of the present invention can be administered to animals prior to infection in order to prevent infection (i.e., as a preventative vaccine), or can be administered to animals after infection in order to treat disease caused by the parasitic nematode (i.e., as a therapeutic vaccine), or both techniques may be used.

Therapeutic compositions of the present invention preferably are formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include, m- or o-cresol, formalin and benzyl alcohol. Standard formulations can either be liquid injectables or solids that can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), inter 10 (IL-10), interleukin 12 (L-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein. In addition to the foregoing adjuvants, when an isolated nucleic acid molecule of the present invention is used as a protective compound in the therapeutic composition, one or more DNA adjuvants can be operatively linked to that nucleic acid molecule using molecular biology techniques known to those skilled in the art.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, gels (including hydrogels), bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain dose levels of the composition effective to protect an animal from disease caused by parasitic nematodes. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions in an effective manner include the specification of individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, intraocular, transdermal and intramuscular routes.

According to one embodiment, a nucleic acid molecule of the present invention can be administered to a host animal in a fashion enabling expression of that nucleic acid molecule into a protective protein or protective RNA (e.g., antisense RNA, ribozyme, triple helix forms or RNA drug) in the host animal. Nucleic acid molecules can be delivered to an animal using a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule.packaged as a recombinant virus vaccine or as a recombinant cell vaccine (i.e., the nucleic acid molecule is delivered by a viral or cellular vehicle)).

A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a bicistronic recombinant molecule, having, for example, one or more internal entry sites. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal, intraocular and oral routes of administration being preferred. A preferred single dose of a naked nucleic acid vaccines ranges from about 1 nanogram (ng) to about 100 $\mu$g, depending on the route of administration and method of delivery, as can be determined by those skilled in the art. Suitable delivery methods include, for example, by injection, as drops, by aerosolization and by topical application. Naked DNA of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging-deficient, encodes an attenuated virus, or both. A number of recombinant viruses can be used including, but not limited to, those based on alphaviruses, poxviruses, adenoviruses, herpesviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines is disclosed in PCT Publication No. WO 94/17813, by Xiong et al., published Aug. 18, 1994, which is incorporated by reference herein in its entirety. An example of methods to produce and use racoon poxvirus recombinant virus vaccines is disclosed in U.S. Pat. No. 5,266,314, to Esposito, et al., issued Nov. 30, 1993, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic nematode as disclosed herein. For example, a recombinant virus vaccine comprising a parasitic nematode transglutaminase nucleic acid molecule of the present invention is administered according to a protocol that results in the animal producing a sufficient immune response to protect itself from disease caused by a parasitic nematode. A preferred single dose of a recombinant virus vaccine of the present invention is from about $1\times10^4$ to about $1\times10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include *Salmonella, E. coli,* Listeria, Mycobacterium, *S. frugiperda,* yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from disease caused by a parasitic nematode can be tested in a variety of ways including, but not limited to, detection of protective antibodies (using, for example, proteins or mimetopes of the present invention), detection of cellular immunity within the treated animal, or challenge of the treated animal with the parasitic nematode to determine whether the treated animal is resistant to disease. Challenge studies can include implantation of chambers including parasitic nematode larvae into the treated animal, or direct administration of larvae to the treated animal, or both. In one embodiment, therapeutic compositions can be tested in animal models such as mice. Such techniques are known to those skilled in the art.

One preferred embodiment of the present invention is the use of parasitic nematode transglutaminase proteins, nucleic acid molecules, antibodies and inhibitory compounds of the present invention, to protect an animal from heartworm. It is particularly preferred to prevent L3 that are delivered to the animal by the mosquito intermediate host from maturing into adult worms. Preferred therapeutic compositions are those that are able to inhibit at least one step in the portion of the parasite's development cycle that includes L3, third molt, L4, fourth molt, immature adult prior to entering the host animal's tissues or circulatory system. In dogs, this portion of the development cycle is about 70 days. Particularly preferred therapeutic compositions include nematode transglutaminase-based therapeutic compositions of the present invention, particularly because *D. immitis* transglutaminase is necessary for *D. immitis* larval molting and development, as disclosed herein. These preferred therapeutic compositions include nematode transglutaminase nucleic acid molecules, nematode transglutaminase proteins and mimetopes thereof, anti-nematode transglutaminase antibodies, and inhibitors of nematode transglutaminase activity that fail to substantially inhibit host animal transglutaminase activity. Particularly preferred are *D. immitis* forms of any of the therapeutic compositions of the present invention. Therapeutic compositions are administered to animals in a manner effective to protect the animals heartworm. Additional protection may be obtained by administering additional protective compounds, including other nematode proteins, nucleic acid molecules, antibodies and inhibitory compounds, as disclosed herein and elsewhere.

One therapeutic composition of the present invention includes an inhibitor of nematode transglutaminase activity that does not substantially inhibit host animal transglutaminase activity. In other words, in one embodiment, a therapeutic composition of the present invention includes a compound capable of substantially interfering with the function of a nematode transglutaminase susceptible to inhibition by an inhibitor of nematode transglutaminase activity. The term, "substantially interfering with the function of nematode transglutaminase," as used herein, refers to the ability of an inhibitor compound to interfere with a nematode transglutaminase activity to such a degree that molting an development of nematode larvae are impaired. For example, an isolated protein or mimetope thereof, is administered in an amount and manner that elicits (i.e., stimulates) an immune response that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of parasitic nematode transglutaminase proteins in order to interfere with development of parasitic nematodes targeted in accordance with the present invention.

An inhibitor of nematode transglutaminase activity can be identified using parasitic nematode transglutaminase proteins of the present invention. One embodiment of the present invention is a method to identify a compound that is capable of inhibiting nematode transglutaminase activity, but that does not substantially inhibit host animal transglutaminase activity. Such a method includes the steps of (a) contacting (e.g., combining, mixing) an isolated nematode transglutaminase protein with a putative inhibitory compound under conditions in which, in the absence of the compound, the protein has nematode transglutaminase activity; (b) determining if the putative inhibitory compound inhibits the nematode transglutaminase activity; and (c) repeating steps (a) and (b), but substituting host animal transglutaminase for nematode transglutaminase. Putative inhibitory compounds to screen for include small organic molecules, antibodies (including fragments and mimetopes thereof) and substrate analogs. Methods to determine nematode and host animal transglutaminase activities are known to those skilled in the art; see, for example, citations in background section and references included therein.

The present invention also includes a test kit to identify a compound capable of inhibiting nematode transglutaminase activity of a parasitic nematode. Such a test kit includes an isolated nematode transglutaminase protein having transglutaminase activity and a means for determining the extent of inhibition of transglutaminase activity in the presence of (i.e., effected by) a putative inhibitory compound. Compounds determined to inhibit nematode transglutaminase activity are also screened to identify those that are not substantially toxic to host animals.

Nematode transglutaminase inhibitors isolated by the method or by the test kit described, or by both, can be used to inhibit any nematode transglutaminase that is susceptible to such an inhibitor. Preferred parasitic nematode transglutaminase proteins to inhibit are those produced by *D. immitis*, *B. Malayi* or *O. volvulus*. A particularly preferred transglutaminase inhibitor of the present invention is capable of protecting an animal from heartworm. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic nematodes. Such diagnostic reagents can be supplemented with additional compounds that can detect other phases of the parasite's life cycle. Methods to use such diagnostic reagents to diagnose parasitic nematode infection are well known to those skilled in the art. Suitable and preferred parasitic nematodes to detect are those to which therapeutic compositions of the present invention are targeted. A particularly preferred parasitic nematode to detect using diagnostic reagents of the present invention is *Dirofilaria immitis*.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references. Further, it should be noted that because sequencing technology is not entirely error-free, the sequences disclosed in the following examples represent apparent amino acid and nucleic acid sequences of parasitic nematode transglutaminase molecules.

Example 1

This example describes a novel N-terminal amino acid sequence of a transglutaminase purified from *Brugia malayi*. This example further describes the use of a protein encoded by that sequence to purify and partially characterize a rare and novel transglutaminase protein from *Dirofilaria immitis*.

Purification and partial characterization of a novel transglutaminase protein from *B. malayi* has been previously described. See, Singh, et al., 1994, *Eur J. Biochem.*, 225, 625–634. A protein molecule corresponding to the N-terminal sequence of the previously described 56-kD transglutaminase of *B. malayi* was synthesized commercially and is herein denoted as $PBmTG_{20}$. The amino acid sequence of this protein, referred to as SEQ ID NO:1, is herein disclosed for the first time as follows:

(D)(G)DVMKFTDADFKE(G)IK(X)(Y)(D)

The amino acids in brackets are the most probable amino acids at those positions, and the amino acid (X) at position 18 could not be detected. A cysteine residue was added toward the N-terminus of the synthetic peptide for the convenience of its conjugation with the carrier protein keyhold limpet hemocyanin (KLH) via maleimidobenzoyl-N-hydroxysuccinimide ester (MBS). 5.0 mg of KLH in 50 mM phosphate buffer, pH 8.0, was reacted with MBS (dissolved in dimethyl sulfoxide) at a molar ratio of 1 KLH:40 MBS. The solution was stirred for 30 min at room temperature. The unreacted MBS was removed by gel filtration, and 5.0 mg of peptide hapten was added to the MBS-activated KLH in 50 mM phosphate buffer, pH 7.5. The solution was stirred at room temperature for 3 hr. Unconjugated peptide was removed by gel filtration. The conjugation efficiency was 40%.

Anti-*B. malayi* transglutaminase peptide PBmTG$_{20}$ antisera was produced as follows. A rabbit was immunized subcutaneously, first with approximately 150 μg of the conjugated peptide mixed with Complete Freund's Adjuvant, and then with five subsequent immunizations of the same dose mixed in Incomplete Freund's Adjuvant. Bleeding and immunization were performed at alternate weeks. Unused antisera were preserved in 0.1% sodium azide at 4° C. For immobilizing the anti-peptide antibodies on Affigel-10 (available from Bio-Rad Laboratories, Hercules, Calif.), the immunoglobulin G (IgG) fraction from this antisera was collected by 40% ammonium sulfate precipitation. Ammonium ions were removed on a NAP-25 column (Sephadex G-25 available from Pharmacia Biotechnology, Piscataway, N.J.) preequilibrated with 100 mM (3-[N-morpholino]propanesulfonic acid) (MOPS) buffer, pH 7.5 (buffer A) to obtain a desalted IgG fraction.

A crude *D. immitis* extract preparation was prepared as follows. All operations were performed at 4° C. unless otherwise mentioned. Thirty-two frozen adult female worms of *D. immitis* (available from TRS laboratories, Athens, Ga.) were homogenized twice in a Pyrex homogenizer in 20 mM Tris-HCl (pH 8.5) containing 0.1% Triton X-100, 2 mM 1,4-dithiothreitol, 1 mM EDTA, 1 mM phenylmethylsulfonyl fluoride (PMSF), and 0.1 mM N-tosyl-L-lysine chloromethane. The resulting 40 ml of homogenate was sonicated as detailed earlier (Singh et al., ibid.). The extract was frozen and thawed between sonications to maximize the solubilization of membrane-bound enzyme. The extract was centrifuged at 15,000 g for 20 min, and the supernatant (36 ml) was collected for further purification.

Anti-*B. malayi* peptide PBmTG$_{20}$, antiserum produced as described above, was found to react with a 56-kD protein band in a western blot of a *D. immitis* extract. This reactivity of anti-PBmTG$_{20}$ antiserum could be completely inhibited in the presence of excess synthetic peptide. In order to monitor the progress of the purification process, Western blots were performed on samples of the extract after each major step in the purification process as follows: Sodium dodecyl sulfate (SDS)-polyacrylamide (10%) gel electrophoresis was performed according to the method of Laemmli (1970). Western blotting was performed by transferring the protein bands to the nitrocellulose paper (0.47 μM, available from Schleicher & Schuell, Keene, N.H.). using the Semiphor dry blot apparatus (available from Hoefer Scientific Instruments, San Francisco, Calif.). All solutions used for membrane processing were made in phosphate buffered saline (PBS), and incubations were done at room temperature unless otherwise noted. The membrane was blocked with 5% nonfat dry milk for 1 hr. and incubated for 1 hr with 1000-fold diluted anti-PBmTG$_{20}$ antiserum in 5% nonfat dry milk. After two washes with 100 ml of PBST (PBS containing 0.1% Tween 20) for 20 min each, the membrane was incubated for 1 hr with 5000-fold diluted alkaline phosphatase-linked anti-rabbit IgG (available from Kirkegaard and Perry Laboratories, Gaithersburg, Md.) in 5% nonfat dry milk. After two washes in 100 ml of PBST for 20 min each, the membrane was treated with alkaline phosphatase color development reagent (available from Bio-Rad Laboratories, Hercules, Calif.) as per manufacturer's instructions.

Following crude extract preparation, the first step in *D. immitis* transglutaminase protein purification was thermoprecipitation and ammonium sulfate precipitation as follows. The crude extract from adult female worms was subjected to thermo-precipitation at 55° C. in a water bath for 10 min with constant shaking. The precipitate was discarded by centrifugation at 15,000 g for 20 min, and the supernatant (31 ml) was precipitated at a 60% ammonium sulfate cutoff. The precipitate was collected by centrifugation (15,000 g for 30 min) and was dissolved in 2.5 ml of buffer A. The ammonium ions in the preparation were removed by passing the preparation through an NAP-25 column preequilibrated with buffer A. The final volume of the *D. immitis* preparation obtained from the NAP-25 column was 3.5 ml.

The next step in *D. immitis* transglutaminase protein purification, immunoaffinity chromatography, was accomplished as follows. The immunoglobulin fraction thus obtained was conjugated to Affigel-10 according to the manufacturer's instructions. About 3.5 ml of the desalted IgG fraction containing anti-*B. malayi* transglutaminase PBmTG$_{20}$ (containing 17.5 mg of protein), obtained as described above in this Example, was added to 1 ml of Affigel-10 that was previously washed with cold deionized water. The suspension was incubated and rotated overnight at 4° C. Next day, the unbound IgG was removed by repeated washing with buffer A.

The 3.5 ml *D. immitis* preparation obtained after ammonium sulfate precipitation and desalting was incubated and rotated with the IgG-bound Affigel-10 overnight at 4° C. The slurry was then packed in a column, and the gel was washed extensively with buffer A. Nonspecifically bound proteins were removed by washing the gel with 0.5% Triton X-100 in buffer A to remove the nonspecific hydrophobic interactions. This step was necessary before the specific elution of transglutaminase at pH 2.8. The gel was washed again with buffer A. *D. immitis* transglutaminase was eluted with 3 ml of 100 mM glycine-HCl buffer (pH 2.8) with a flow rate of 10 ml/hr. The pH of the *D. immitis* transglutaminase-containing collected fraction was immediately adjusted to pH 8.0 by adding 300 μl of 1 M sodium bicarbonate; the collected fraction was then subjected to overnight dialysis against 100 mM Tris-HCl buffer (pH 8.5). The dialyzed fraction was concentrated to 0.5 ml in a Centricon-10 tube (available from Pharmacia Biotechnology Piscataway, N.J.), and used for further characterization.

The eluted protein was enzymatically active and gave a single major band of 56-kD when subjected to eletrophoresis under denaturing conditions. The same band 56 kD band was detected by western blot analysis (described below) when the anti-*B. malayi* transglutaminase peptide PBmTG$_{20}$ antibody was used to detect protein.

A summary of the steps used in the purification of transglutaminase from *D. immitis* is shown in Table 1. The starting transglutaminase activity in 224 mg of initial soluble protein obtained from 32 adult female worms was extremely low. The specific activity in the crude extract obtained from *D. immitis* was at least 5 times lower than that previously reported for *B. malayi* transglutaminase preparation (Singh et al., ibid.).

Transglutaminase activity was determined in a microtiter plate assay according to a recently published procedure; see, Slaughter et al., 1992, *Anal. Biochem.* 205, 166–171. One milliunit (mU) transglutaminase activity is defined as the $V_{max}$ ($\Delta A_{405}$/min) generated in a microtiter plate assay by 0.74 μg of purified guinea pig liver transglutaminase (available from Sigma Chemical Co., T-5398). The effects of pH and temperature on the transglutaminase activity and stability as well as the effects of inhibitors, metal ions and other cofactors on the enzyme activity were determined as described by Singh et al., ibid. The amount of protein was estimated according to the Bradford method (see Bradford, 1976, *Anal. Biochem.*, 72, 248–254), using reagents available from Bio-Rad Laboratories, Hercules, Calif.

TABLE 1

Summary of steps used for the purification of transglutaminase from *D. immitis* adult worms.

| Steps | Total protein (μg) | Total volume (ml) | Total activity (mU) | Specific activity (mU/mg) | Cumulative fold purification | Yield (%) |
|---|---|---|---|---|---|---|
| 1. Crude extract | 224,200 | 36.0 | 42.6 | 0.19 | 1.0 | 100 |
| 2. Thermoprecipitation | 129,634 | 31.0 | 35.0 | 0.27 | 1.4 | 82 |
| 3. $(NH_4)_2SO_4$ precipitation | 11,157 | 3.5 | 26.8 | 2.33 | 12.2 | 63 |
| 4. Immunoaffinity chromatography | 2.1 | 0.5 | 4.2 | 2032.0 | 10,694.0 | 10 |

The *D. immitis* transglutaminase protein preparation protocol presented here resulted in a high degree of purification of *D. immitis* transglutaminase. The final product was approximately 5 times purer than that previously reported for *B. malayi* transglutaminase purified by the lengthy conventional protocol of Singh et al., ibid. The specific activity of the purified *D. immitis* enzyme was 2.0 U/mg protein, and is very close to that previously reported for *B. malayi* transglutaminase. Although the enzyme was stable over a wide pH range (data not shown), it was most active in the basic pH range, between pH 8 and pH 9.5, as are the other transglutaminases. In contrast to mammalian transglutaminases, the *D. immitis* enzyme, like the transglutaminase isolated from *B. malayi* (see, Singh, et al., ibid.) was active and stable at high temperatures (data not shown).

The effects of various reagents on the activity of the transglutaminase purified from adult *D. immitis* worms is shown in Table 2. The enzyme required calcium for its activity, and chelating agents like EGTA and EDTA completely blocked the activity. Dithiothreitol and mercaptoethanol increased the enzyme activity substantially, whereas iodoacetamide decreased the activity drastically, suggesting that the enzyme requires at least one cysteine residue at the active site, like most of the transglutaminases; see, for example, Folk et al., 1977, *Adv. Protein Chem.* 31, 1–133. The effect of iodoacetamide was severe when the enzyme was pretreated with calcium ions, suggesting that calcium ions open the active site for high molecular weight substrates like casein. The enzyme was inhibited competitively by amine donor substrate analogues like monodansyl cadaverine and putrescine, and by the active-site inhibitor cystamine. High concentrations of sodium and potassium ions, Tris and the end product of the reaction, ammonia, reversibly inhibited the enzyme. The observation that Cbz-Gln-Gly affects the enzyme activity only slightly (Table 2) suggests that this compound is a poor amine acceptor substrate for the enzyme. In contrast to mammalian tissue type transglutaminases (Folk et al., ibid.; Bergamini et al., 1987, *Biochim. Biophys. Acta* 916, 149–151; Achyuthan et al., 1987, *J. Biol. Chem.* 262, 1901–1906; Bergamini, 1988, *FEBS Lett.* 239, 255–258; Lee et al., 1989, *Biochem. Biophys. Res. Commun.* 162, 1370–1375), this enzyme was not affected adversely by micromolar concentrations of GTP. This suggests that GTP is not involved in the regulation of this enzyme as in nematode transglutaminase from *B. malayi* (Singh et al., ibid.) and Limulus hemocyte transglutaminase (Tokunaga et al., 1993, *J. Biol. Chem.* 268, 252–261).

TABLE 2

Effect of ions, inhibitors and other reagents on *D. immitis* transglutaminase activity

| Reagent* | Concentration (mM) | Transglutaminase activity† (% of control) |
|---|---|---|
| Control‡ | — | 100 |
| NaCl | 500 | 48 |
| KCl | 500 | 54 |
| $(NH_4)_2SO_4$ | 10 | 0 |
| EDTA | 10 | 0 |
| EGTA | 10 | 0 |
| Iodoacetamide ($-Ca^{2++}$)§ | 10 | 61 |
| Iodoacetamide ($+Ca^{2++}$)¶ | 10 | 27 |
| Tris-HCl (pH 8.5) | 250 | 66 |
| Tris-HCl (pH 8.5) | 500 | 40 |
| Nα-CBZ-Gln-Gly | 10 | 92 |
| Monodansyl cadaverine | 1 | 9 |
| Putrescine | 1 | 14 |
| Cystamine | 1 | 52 |
| GTP | 0.1 | 100 |
| GTP | 1 | 95 |

*The effect of metals, ions and other reagents on transglutaminase activity was determined in the presence of $CaCl_2$ and dithiothreitol.
†The results shown are the average values from two independent experiments each performed in triplicate. Standard deviation from the mean was less than 5%.
‡Control tubes contained 10 mM $CaCl_2$ and 10 mM dithiothreitol.
§Iodoacetamide was preincubated with the enzyme in the absence of calcium overnight at 4° C., and the activity was determined in the presence of 10 mM each of calcium and dithiothreitol after removal of iodoacetamide by dialysis.
¶Iodoacetamide was preincubated with the enzyme in the presence of 10 mM calcium ovenight at 4° C., and the activity was determined in the presence of 10 mM each of calcium and dithiothreitol after removal of iodoacetamide by dialysis.

Example 2

This Example evaluated the effect of a number of transglutaminase inhibitors on *D. immitis* larval viability in an in vitro larval culture system.

The following transglutaminase inhibitors were tested at the indicated final concentrations in the culture system:

(a) Monodansyl cadaverine (MDC), a known high affinity substrate analog was tested at concentrations of 25, 50, 75, 85 and 100 μM;

(b) Cystamine, a transglutaminase active site inhibitor was tested at concentrations of 25, 50, 75, 85 and 100 μM;

(c) Iodoacetamide was tested at concentrations of 2.5, 5 and 10 μM.

All inhibitors are available from Sigma Chemical Co, St. Louis, Mo. Inhibitors were made in NI media (50% NCTC+

50% IMDM, available from GibcoBRL, Gaithersburg, Md.) containing antibiotics and 20% SeruMax (available from Sigma Chemical Co. St. Louis, Mo.).

The general protocol for the larval viability assays was as follows: Briefly, 50 D. immitis $L_3$ larvae were cultured for 6 days in vitro in 1 ml of NI media containing antibiotics and 20% SeruMax (available from Sigma Chemical Co. St. Louis, Mo.). In some assays, transglutaminase inhibitors were added on different days of culture, and in other assays the inhibitors were present for only 24 hours of culture. The cultures were examined microscopically every 24 hours until day 6 when the cultures were terminated. The number of larvae that molted were determined by counting shed cuticles.

Results of these studies are presented below in Tables 3, 4, and 5. All transglutaminase inhibitors tested in the present study reduced in a dose-dependent manner the molting of D. immitis $L_3$ larvae to $L_4$ larvae (Table 3).

TABLE 3

Effect of TGase inhibitors on molting of Dirofilaria immitis $L_3$

| Inhibitor | Concentration (µM) | Percent molted |
| --- | --- | --- |
| Monodansylcadaverine (MDC) | 0 | 84 |
|  | 25 | 75 |
|  | 50 | 63 |
|  | 75 | 28 |
|  | 85 | 2.5 |
|  | 100 | 0 |
| Cystamine | 0 | 84 |
|  | 25 | 61 |
|  | 50 | 62 |
|  | 75 | 17 |
|  | 85 | 1 |
|  | 100 | 0 |
| Iodoacetamide | 0 | 84 |
|  | 2.5 | 65 |
|  | 5 | 3 |
|  | 10 | 0 |

MDC and cystamine at 100 µM final concentration completely inhibited the molting process; Iodoacetamide at a final concentration of 10 µM was able to inhibit the molting of $L_3$ to $L_4$. In each case, complete inhibition of D. immitis molting required the presence of inhibitors during the first 24–48 hr of the molting process (Tables 4 and 5). The transglutaminase active site inhibitor (cystamine) was a very effective inhibitor of larval molting even when added on day 2 during the culture (Table 5).

TABLE 4

Presence of TGase inhibitors during first 24 hr of D. immitis $L_3$ culture-Effect on molting

| Inhibitor | Concentration (µM) | Percent molted |
| --- | --- | --- |
| Monodansylcadaverine (MDC) | 0 | 68 |
|  | 50 | 64 |
|  | 100 | 41 |
| Cystamine | 0 | 68 |
|  | 50 | 68 |
|  | 100 | 13 |
| Iodoacetamide | 0 | 68 |
|  | 10 | 3 |

TABLE 5

Molting of D. immitis $L_3$ in presence of TGase inhibitors added to culture on different days.

| Inhibitor | Day added | Percent molted |
| --- | --- | --- |
| Monodansylcadaverine* (MDC) | 0 | 0 |
|  | 1 | 18 |
|  | 2 | 78 |
| Cystamine* | 0 | 0 |
|  | 1 | 0 |
|  | 2 | 10 |
| Iodoacetamide* | 0 | 0 |
|  | 1 | 0 |
|  | 2 | 82 |
| None |  | 70 |

*MDC and Cystamine were used at a concentration of 100 µM
†Iodoacetamide was used at a 10 µM concentration Example 3

This example demonstrates that soluble adult and larval D. immitis parasite extracts contain transglutaminase activity.

Larval and adult male and female heartworm parasites were separately homogenized in buffer B (20 mM Tris/HCl pH 8.5, containing 2 mM 1,4-dithiothreitol, 2 mM EDTA, 1 mM Phenylmethylsulfonyl fluoride, 0.1 mM N-tosyl-L-lysine chloromethane and 0.1 mM N-tosyl-L-phenylalanine chloromethane; all available from Sigma) for 20 min on ice. The crude extracts thus obtained were sonicated continuously for three 1-min periods, with 5-min intervals between each sonication, using a pre-chilled small probe of the W-380 Ultrasonic Processor (available from Heat Systems-Ultrasonics, Farmingadale, N.Y.). The third sonication was done in the presence of 0.1% Triton X-100. The suspensions were centrifuged at 15,000×g for 20 min. The supernatants thus obtained (referred to herein as the parasite extracts, or crude parasite extracts) was used to assay for transglutaminase activity.

Transglutaminase activity was determined in a microtiter plate assay as described above in Example 1. In brief, the microtiter plates were coated with 1% dimethylcasein (available from Sigma) at room temperature overnight; uncoated sites were blocked with 1% nonfat dry milk. The reaction mixtures contained in total volumes of 200 µl each: 100 mM Tris/HCl pH 8.5, 10 mM $CaCl_2$, 10 mM dithiothreitol, 1 mM amine donor substrate 5(biotinamido) pentylamine (BPT), (available from Sigma), and crude parasite extracts. The reactions were performed at 37° C. for 2 hours and transglutaminase-catalyzed conjugation of BPT into dimethylcasein was determined by streptavidin-peroxidase and orthophenyldiamine as a reporter system. The enzyme activity (expressed as mU) in extracts was determined relative to the activity of purified guinea pig liver transglutaminase (available from Sigma) tested in the same microtiter plate. The results of this assay are given in Table 6. There was detectable transglutaminase activity both in larval and adult extracts. The activity in males was lower than in females for the same amount of protein tested.

TABLE 6

Transglutaminase enzyme activity in *D. immitis* larvae and adults

| Parasite stage | Amount used | Total activity (mU) |
| --- | --- | --- |
| 0 hr $L_3$ | 100 $L_3$ | 38.9 |
| 48 hr $L_3$ | 100 $L_3$ | 42.3 |
| 6 day $L_4$ | 100 $L_4$ | 27.6 |
| Male adult | 60 μg | 9.0 |
| Female adult | 60 μg | 50.0 |

Example 4

This example describes the identification of native *D. immitis* transglutaminase (DiTG) by immunoblot analysis. Rabbit anti-*B. malayi* transglutaminase peptide PBmTG$_{20}$ antisera, produced as described in Example 1, was used to identify a native *D. immitis* transglutaminase protein in *D. immitis* extracts as follows.

The material in crude extracts from *D. immitis* larvae and adult male and female worms were separated by running 5 μg protein per lane on a 12-well 10% Tris-glycine SDS-PAGE gel at 200 volts for 1 hour, and then transferred to a nitrocellulose membrane by standard methods. After transfer, the membrane was blocked in 5% dry milk for 1 hr at 37° C. The membrane was then incubated with rabbit anti-*B. malayi* transglutaminase peptide PBmTG$_{20}$ antibody at a dilution of 1:2500 in Tris buffered saline. After 1 hr incubation at room temperature, the blot was washed, and antibody binding resolved using a peroxidase-labeled rabbit IgG secondary antibody and the substrate nitroblue tetrazolium chloride, 5-bromo-4-chloro-3-indolylphosphate p-toluidine salt (NBT/BCIP) (available from Gibco BRL, Gaithersburg, Md.). Using this antibody, immunoblot analysis of *D. immitis* adult male, female and larval extracts identified a 56 kD native *D. immitis* protein (DiTG) similar to the size of native Brugia protein (Singh et al., ibid.).

Example 5

This example describes the amino acid sequence analysis of the 56 kD *D. immitis* transglutaminase.

The native 56 kD *D. immitis* transglutaminase protein from adult female *D. immitis* parasite extracts was separated by two dimensional SDS-PAGE. The first dimension was an isoelectric focusing gel using a non-equilibrium pH gradient containing ampholines of pI 5–8 (available from Pharmacia Biotech, Uppsala, Sweden). The second dimension was run on an 8% Tris-glycine gel; the resulting protein spots were transferred to PVDF membrane, and the spot corresponding to *D. immitis* transglutaminase was excised. 17 such spots were then used for N-terminal sequence analysis using an automated protein sequencer (ABI437A, available from Applied Biosystems, Inc., Foster City, Calif.).

For internal amino acid sequence analysis, spots containing *D. immitis* transglutaminase were excised from Coomassie blue stained preparative two dimensional SDS-PAGE gels of female *D. immitis* parasite extract. 48 such spots were pooled and then subjected to trypsin digestion in the gel. The digested protein sample was then separated using high pressure liquid chromatography (HPLC). Digested proteins were then sequenced as described above. Preparation and sequencing of the internal protein fragments were performed by the Harvard Microchemistry Facility, Cambridge, Mass.

The results of the amino acid sequence analysis of *D. immitis* transglutaminase are given below. A partial N-terminal amino acid sequence of about 29 amino acids was determined and is represented herein as SEQ ID NO:2:

D G D V M K F T D A D F K E G I K P Y D V L L V K F Y A P

A homology search of a non-redundant protein sequence database was performed on this amino acid sequence through the National Center for Biotechnology Information (NCBI) (National Library of Medicine, National Institute of Health, Baltimore, Md.) using the BLAST network. This database includes SwissProt+PIR+SPupdate+GenPept+GPUpdate+PDB databases. The search was performed using SEQ ID NO:2 and showed significant homology to probable protein disulfide isomerases (PDIs) spanning from amino acid residue 1 through 29 of SEQ ID NO:2. The highest scoring match of the homology search at the amino acid level was GenBank™ accession number Z37139, *Caenorabditis elegans* clone C14B1.1. SEQ ID NO:2 showed about 44% identity to residues 24 to 50 of the clone C14B1.1. SEQ ID NO:2 also showed a near sequence identity to the *B. malayi* peptide, PBmTG$_{20}$, SEQ ID NO:1.

The two internal *D. immitis* transglutaminase amino acid sequences obtained as described above were characterized as follows: A partial internal amino acid sequence of about 14 amino acids was determined and is represented herein as SEQ ID NO:3:

Y Q Y D L L P M F V V Y G K

A homology search of a non-redundant protein sequence database was performed on SEQ ID NO:3 through the NCBI using the BLAST network as described above. This database includes SwissProt+PIR+SPupdate+GenPept+GPUpdate+PDB. Results of the search showed no significant homology of SEQ ID NO:3 to other proteins in the database.

Another partial internal amino acid sequence of about 19 amino acids was determined and is represented herein as SEQ ID NO:4:

M D A T A N D V P P P F Q V Q G F P T

A homology search of a non-redundant protein sequence database was performed on this amino acid sequence using the BLAST network through the NCBI, as described above. The search was performed using SEQ ID NO:4 and showed significant homology to probable PDIs spanning from amino acid residue 1 through 19 of SEQ ID NO:4. The highest scoring match of the homology search at the amino acid level was GenBank™ accession number PC1298 (chicken nuclear matrix 57 K protein). SEQ ID NO:4 showed about 78% identity to residues 42 to 60 of this chicken nuclear matrix protein sequence.

Example 6

This example describes the isolation and sequencing of a nucleic acid molecule encoding a *D. immitis* transglutaminase protein.

A *D. immitis* transglutaminase nucleic acid molecule of about 707 nucleotides, denoted nDiTG$_{707}$, was identified by polymerase chain reaction (PCR) from *D. immitis* first strand cDNA reverse transcribed from adult female mRNA as follows. The following primers were used to PCR amplify the *D. immitis* transglutaminase nucleic acid molecule from the cDNA template: A sense primer spanning nucleotides encoding amino acid residue number about 5 through amino acid residue number about 15 of SEQ ID NO:2, and having the nucleic acid sequence 5'ATGAARTTYACNGAYGCN-GAYTTYAARGARGG 3' (denoted herein as SEQ ID NO:15); and an anti-sense primer spanning nulceotides encoding amino acid residue number about 8 through amino acid residue number about 14 of SEQ ID NO:3 and having the nucleic acid sequence 5'TTNCCRTANACNACRAA-CAT 3' (denoted herein as SEQ ID NO:16).

The PCR amplified *D. immitis* transglutaminase nucleic acid molecule, referred to herein as nDiTG$_{707}$, was separated from the rest of the PCR reaction products on a 1% agarose gel at 60 v for 2 hr. After separation of the PCR products, the band of interest was excised from the agarose gel. The gel slice was then processed to release the DNA using the QIAquick kit (available from Qiagen, Chatsworth, Calif.) as per manufacturer's instructions. The purified DNA was then cloned into TA cloning vector (available from Invitrogen, San Diego, Calif.) as per the manufacturer's instructions and submitted for automated sequence analysis. The sequences of the two complementary strands of nDiTG$_{707}$ are presented as SEQ ID NO:5 and SEQ ID NO:7.

Translation of SEQ ID NO:5 yields a protein of about 235 amino acids, denoted PDiTG$_{235}$, the amino acid sequence of which is presented in SEQ ID NO:6. The nucleic acid molecule encoding PDiTG$_{235}$ is referred to herein as nDiTG$_{705}$, the nucleic acid sequence of which is represented in SEQ ID NO:8 (the coding strand) and SEQ ID NO:9 (the complementary strand). Based on its amino acid sequence, PDiTG$_{235}$ has a predicted molecular weight of about 27.2 kD and an estimated pI of about 5.07.

Amino acid sequence of PDiTG$_{235}$ (i.e. SEQ ID NO:6) was analyzed using the PC/GENE (available from Intelligenetics, Inc., Mountainview, Calif.) sequence analysis program for sites and signatures. A thioredoxin family active site was detected from residues about 24 to 30. Thioredoxins participate in various redox reactions through the reversible oxidation of an active center disulfide bond; see, for example, Holmgren, ibid. A number of eukaryotic proteins contain similar domains evolutionarily related to thioredoxin.

A homology search of a non-redundant protein sequence database was performed through the NCBI using the BLAST network, as described above. The search performed using SEQ ID NO:6 showed that this sequence has significant homology to protein disulfide isomerases (PDI), and PDI-related proteins, of eukaryotic origin. The homology spans from about amino acid 1 through about amino acid 235 of SEQ ID NO:6. The highest scoring match of the homology search at the amino acid level was GenBank™ accession number P38658, *Schistosoma mansoni*, probable PDI ER-60 precursor. SEQ ID NO:6 showed about 37% identity to P38658. At the nucleotide level, the coding regions represented in SEQ ID NO:8, from nucleotide 7 to 246, were similar to that of the human clone PA3 (GenBank™ accession number J05016), PDI-related protein (Erp72) mRNA. SEQ ID NO:8 showed about 59% nucleic acid identity spanning from nucleotide 589 to 828 of clone PA3.

Example 7

The following experiment was performed in order to confirm the *D. immitis* origin of the isolated DiTG cDNA nucleic acid molecule nDiTG$_{707}$, and in order to identify the genomic restriction fragments corresponding to nDiTG$_{707}$. A Southern blot containing about 10 µg of EcoRI and XhoI restricted *D. immitis* genomic DNA was hybridized under stringent conditions with nDiTG$_{707}$ DNA labeled with a chemiluminescent label (ECL labeling kit, available from Amersham, Arlington Heights, Ill.). The probe detected a single band of about 11.7 kilobase pairs (kb) in the genomic DNA digested with XhoI, where as in EcoRI digested genomic DNA, the probe detected three bands at about 9.5, 1.07 and 0.43 kb, respectively.

Example 8

This example describes the isolation and characterization of transglutaminase nucleic acid molecules of the present invention from a *D. immitis* L$_4$ cDNA library.

*D. immitis* transglutaminase nucleic acid molecules were cloned from a cDNA library by nucleic acid screening using *D. immitis* transglutaminase nucleic acid molecules of the present invention as probes. Specifically, a 48 hour *D. immitis* larval cDNA library was constructed from 229 600 L$_3$ as follows. *D. immitis* L$_3$ larvae were cultured in NCTC 135: IMDM media and 20% Seru-Max™ for 48 hours. Larvae were settled by gravity at 37° C., culture media were removed and larvae were disrupted in 4 M guanidinium thiocyanate, 1.5% sarkosyl, 0.5 M 2-mercaptoethanol. Total RNA was recovered by the acid guanidinium-thiocyanate-phenol-chloroform procedure (Chomczynski, et al., 1987, *Anal. Biochem.* 162, pp. 156–159). Poly A$^+$ mRNA was isolated with oligo(dT) cellulose using the RiboSep Mini mRNA Isolation Kit (available from Collaborative Research, Inc., Bedford, Mass.). The ZAP-cDNA® Synthesis Kit (available from Stratagene, La Jolla, Calif.) was used to synthesize cDNA, which was then ligated into the Uni-ZAP XR vector (Stratagene), packaged and amplified to produce the L$_4$ cDNA library. The nucleic acid molecule, nDiTG$_{707}$, (represented herein by the sequences SEQ ID NO:5 and SEQ ID NO:7) was labeled with a chemiluminescent label as described in Example 7, and used as a DNA probe to screen the L$_4$ cDNA expression library. A clone containing a *D. immitis* transglutaminase nucleic acid molecule referred to herein as nDiTG$_{1472}$ was plaque-purified from the expression library using standard methods, and then sequenced. The following nucleotide primers were used to sequence this clone: a) two pBluescript™ vector primers consisting of a sense T$_3$X primer (denoted herein as SEQ ID NO:17) having the nucleic acid sequence 5'AATTAACCCT-CACTAAAGGG 3'; and an antisense T$_7$X primer (denoted herein as SEQ ID NO:18) having the nucleotide sequence, 5'GTAATACGACTCACTATAGGGC 3'; and b) three internal primers including a sense primer having the nucleic acid sequence 5'GAAAACCGTTATCAGTATGATCT 3' (denoted herein as SEQ ID NO:19), and two antisense primers having the nucleic acid sequences 5'CTGTGGAAT-GATTTAAATATTTATCC 3' (denoted herein as SEQ ID NO:20) and 5'GTCCATTTTTGCAATAACAACACC 3' (denoted herein as SEQ ID NO:21), respectively. The resulting nucleic acid sequences of the two complementary DNA strands of nDiTG$_{1472}$ are referred to herein as SEQ ID NO:10 and SEQ ID NO:12. The sense primer represented by SEQ ID NO:19 spans nucleotides about nucleotide 359 to about nucleotide 381 of SEQ ID NO:10; the antisense primer represented by SEQ ID NO:20 spans about nucleotide 1171 to about nucleotide 1192 of SEQ ID NO:10; and the antisense primer SEQ ID NO:21 spans from about nucleotide 878 to about nucleotide 901 of SEQ ID NO:10

Translation of SEQ ID NO:10 yields a protein of about 368 amino acids, denoted PDiTG$_{368}$, the amino acid sequence of which is presented in SEQ ID NO:11. The nucleic acid molecule encoding PDiTG$_{368}$ is referred to herein as nDiTG$_{1107}$ the nucleic acid sequence of which is represented in SEQ ID NO:13 (the coding strand) and SEQ ID NO:14 (the complementary strand) assuming that the first codon spans from about nucleotide 2 through about nucleotide 5, and a putative stop codon spans from about nucleotide 1106 to about nucleotide 1108 (the stop codon included in nDiTG$_{1107}$). The amino acid sequence of *D. immitis* PDiTG$_{368}$ (i.e., SEQ ID NO:11) predicts that PDiTG$_{368}$ has an estimated molecular weight of about 42.6 kD and an estimated pI of 5.71.

The amino acid sequence of PDiTG$_{368}$ (i.e., SEQ ID NO:11) was analyzed using the PC/GENE program to identify sites and signatures. A number of interesting sites were detected. They include: i) a thioredoxin family active site detected from residues 268 to 274; ii) an endoplasmic reticulum (ER) targeting sequence from residues 365 to 368 (KEEL); proteins that permanently reside in the lumen of ER seem to be distinguished from newly synthesized secretory proteins by the presence of the C-terminal sequence Lys-Asp-Glu-Leu (KDEL); see Munro et al., ibid. *Cell* 48, 899–907; Pelham, ibid.; and iii) a tachykinin family signature from residues 186 to 202 (tachykinins are a group of biologically active peptides that excite neurons, evoke behavioral responses, are potent vasodilators, and contract many smooth muscles; see, Maggio, 1988, *Annual Review of Neurosciences* 11, 13–28).

A homology search of a non-redundant protein sequence database was performed on SEQ ID NO:11 using the BLAST network through the NCBI, as described above. The search showed significant homology to PDI, and PDI-related proteins of eukaryotic origins, spanning from about amino acid 1 through about amino acid 368 of SEQ ID NO:11. The highest scoring match of the homology search at the amino acid level was to GenBank™ accession number D16234 (from amino acid residues 130 to 505), a human phospholipase C-alpha clone. This match revealed about 47% identity spanning amino acid residues about 3 to about 368 of SEQ ID NO:11. The nucleic acid coding region represented in SEQ ID NO:13, from about nucleotide 717 to about nucleotide 1032, was similar to that of human epithelial cell mRNA for ER-60 protease (GenBank™ accession number D83485), being about 63% identitical to nulceotides 1143 through 1458 of the ER-60 protease sequence.

Example 9

This Example describes the PCR amplification and subsequent isolation of transglutaminase nucleic acid molecules from other related filarial parasites. Nematode transglutaminase nucleic acid molecules from *Brugia malayi* and *Onchocerca volvulus* were identified using standard PCR technology and methods as follows. Two primers were used in PCR reactions that represent internal sequences of nDiTG$_{1472}$: a sense primer spanning from about nucleotide 359 to about nucleotide 371 of SEQ ID NO:10, and having the nucleotide sequence 5'GAAAACCGTTATCAGTAT-GATCT 3' (SEQ ID NO:19), and an antisense primer spanning from about nucleotides 878 to 901 of SEQ ID NO:10, and having the nucleotide sequence GTCCATTTTTG-CAATAACAACACC 3' (SEQ ID NO:20). Based on the sequence information provided by nDiTG$_{1472}$, these primers should amplify a DNA sequence of about 542 nucleotides. The primers amplified a molecule of about 542 nucleotides from both *O. volvulus* adult mixed male and female cDNA (denoted herein as nOvTG$_{542}$) and *B. malayi* adult male cDNA (denoted herein as nBmTG$_{542}$) libraries, respectively.

Nucleic acid molecules nOvTG$_{542}$ and nBmTG$_{542}$ were gel purified, cloned into TA cloning vector (available from Invitrogen) and submitted for automated sequencing.

Example 10

This example describes the identification of *D. immitis* poly(A)$^+$ RNA transcripts corresponding to nDiTG$_{707}$.

A Northern blot was performed as follows: *D. immitis* adult female and male total RNA (8 μg) and adult female and male poly(A)+RNA (0.5 μg) were electrophoresed on a 1% formaldehyde gel and transferred to a N+ nylon membrane (available from Amersham). The RNA was cross-linked to the membrane using the Stratalinker (available from Strategene). The Northern blot was then hybridized with peroxidase-labeled nDiTG$_{707}$ cDNA using the ECL direct nucleic acid labeling and detection system (available from Amersham) as per the manufacturer's instructions. In each of the four samples, the nDiTG$_{707}$ cDNA probe hybridized to a single band of approximately 2613 nucleotides as calculated by MacVector's mobility program.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:21 submitted herewith are the same.

SEQUENCE LISTING (1) GENERAL INFORMATION:

(iii) NUMBER OF SEQUENCES:   21

(2) INFORMATION FOR SEQ ID NO:1:

(i) SEQUENCE CHARACTERISTICS:
      (A) LENGTH:  20 amino acids
      (B) TYPE:  amino acid
      (D) TOPOLOGY:  linear (ii) MOLECULE TYPE:  protein (iii) FEATURE:
      (A) NAME/KEY:  Xaa = Unknown
      (B) LOCATION:  18

(vii) SEQUENCE DESCRIPTION:  SEQ ID NO:1:

```
Asp Gly Asp Val Met Lys Phe Thr Asp Ala Asp Phe Lys Glu Gly Ile
 1               5                  10                  15

Lys Xaa Tyr Asp
            20
```

(2) INFORMATION FOR SEQ ID NO:2:

(i) SEQUENCE CHARACTERISTICS:
        (A) LENGTH: 29 amino acids
        (B) TYPE: amino acid
        (D) TOPOLOGY: linear (ii) MOLECULE TYPE: protein (vii) SEQUENCE DESCRIPTION: SEQ ID NO:2:

```
Asp Gly Asp Val Met Lys Phe Thr Asp Ala Asp Phe Lys Glu Gly Ile
 1               5                  10                  15

Lys Pro Tyr Asp Val Leu Leu Val Lys Phe Tyr Ala Pro
            20                  25
```

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: protein (vii) SEQUENCE DESCRIPTION: SEQ ID NO:3:

```
Tyr Gln Tyr Asp Leu Leu Pro Met Phe Val Val Tyr Gly Lys
 1               5                  10
```

(2) INFORMATION FOR SEQ ID NO:4:

(i) SEQUENCE CHARACTERISTICS:
        (A) LENGTH: 19 amino acids
        (B) TYPE: amino acid
        (D) TOPOLOGY: linear (ii) MOLECULE TYPE: protein (vii) SEQUENCE DESCRIPTION: SEQ ID NO:4:

```
Met Asp Ala Thr Ala Asn Asp Val Pro Pro Phe Gln Val Gln Gly
 1               5                  10                  15

Phe Pro Thr
```

(2) INFORMATION FOR SEQ ID NO:5:

(i) SEQUENCE CHARACTERISTICS:
        (A) LENGTH: 707 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1...705

(xi) SEQUENCE DESCRIPTION: SEQ ID NO:5:

```
ATG AAA TTT ACA GAT GCG GAC TTC AAG GAG GGA ATT AAA CCA TAT GAT     48
Met Lys Phe Thr Asp Ala Asp Phe Lys Glu Gly Ile Lys Pro Tyr Asp
 1               5                  10                  15

GTA TTA CTT GTG AAA TTT TAT GCA CCA TGG TGC GGA CAC TGC AAA AAG     96
Val Leu Leu Val Lys Phe Tyr Ala Pro Trp Cys Gly His Cys Lys Lys
```

```
          20                      25                      30
ATA GCA CCA GAA TTT GAA AAA GCA GCA ACC AAA CTT TTA CAG AAT GAT       144
Ile Ala Pro Glu Phe Glu Lys Ala Ala Thr Lys Leu Leu Gln Asn Asp
         35                      40                      45

CCG CCT ATT CAT TTA GCA GAG GTT GAC TGT ACG GAG GAG AAG AAA ACT       192
Pro Pro Ile His Leu Ala Glu Val Asp Cys Thr Glu Glu Lys Lys Thr
         50                      55                      60

TGC GAT GAA TAC GGT GTT AGT GGC TTC CCG ACT TTG AAA ATT TTC CGT       240
Cys Asp Glu Tyr Gly Val Ser Gly Phe Pro Thr Leu Lys Ile Phe Arg
 65                      70                      75                      80

AAG GGA GAA CTA GCA CAG GAT TAT GAT GGT CCG AGA GTA GCA GAA GGT       288
Lys Gly Glu Leu Ala Gln Asp Tyr Asp Gly Pro Arg Val Ala Glu Gly
                 85                      90                      95

ATT GTG AAA TAT ATG CGT GGA CAG GCA GGT CCA TCA GCT ACA GAA ATT       336
Ile Val Lys Tyr Met Arg Gly Gln Ala Gly Pro Ser Ala Thr Glu Ile
                100                     105                     110

AAT ACA CAA CAA GAA TTC GAA AAA ATG TTG CAA GCC GAT GAC GTT ACT       384
Asn Thr Gln Gln Glu Phe Glu Lys Met Leu Gln Ala Asp Asp Val Thr
            115                     120                     125

ATT TGT GGA TTT TTC GAA GAG AAC AGC AAG TTA AAA GAC TCA TTC TTA       432
Ile Cys Gly Phe Phe Glu Glu Asn Ser Lys Leu Lys Asp Ser Phe Leu
        130                     135                     140

AAA GTT GCG GAT ACA GAA AGA GAT CGT TTT AAG TTT GTG TGG ACA TCA       480
Lys Val Ala Asp Thr Glu Arg Asp Arg Phe Lys Phe Val Trp Thr Ser
145                     150                     155                     160

AAT AAA CAA ATT CTG GAA TCA AGG GGA TAC AAT GAT GAT ATC GTC GCA       528
Asn Lys Gln Ile Leu Glu Ser Arg Gly Tyr Asn Asp Asp Ile Val Ala
                165                     170                     175

TAT CAA CCG AAG AAA TTT CAT AAT AAA TTT GAA CCA AAT GAA TTC AAG       576
Tyr Gln Pro Lys Lys Phe His Asn Lys Phe Glu Pro Asn Glu Phe Lys
                180                     185                     190

TAT GAT GGA AAT TAC GAC ACA GAC AAG ATT AAA GAA TTT CTC CTA CAC       624
Tyr Asp Gly Asn Tyr Asp Thr Asp Lys Ile Lys Glu Phe Leu Leu His
            195                     200                     205

GAA ACA AAT GGG CTT GTT GGT ATA CGA ACG GCC GAA AAC CGT TAT CAG       672
Glu Thr Asn Gly Leu Val Gly Ile Arg Thr Ala Glu Asn Arg Tyr Gln
        210                     215                     220

TAT GAT CTA CTT CCG ATG TTC GTC GTC TAT GGC AA                        707
Tyr Asp Leu Leu Pro Met Phe Val Val Tyr Gly
225                     230                     235

(2) INFORMATION FOR SEQ ID NO:6:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Phe Thr Asp Ala Asp Phe Lys Glu Gly Ile Lys Pro Tyr Asp
 1               5                  10                  15

Val Leu Leu Val Lys Phe Tyr Ala Pro Trp Cys Gly His Cys Lys Lys
                20                  25                  30

Ile Ala Pro Glu Phe Glu Lys Ala Ala Thr Lys Leu Leu Gln Asn Asp
            35                  40                  45

Pro Pro Ile His Leu Ala Glu Val Asp Cys Thr Glu Glu Lys Lys Thr
        50                  55                  60

Cys Asp Glu Tyr Gly Val Ser Gly Phe Pro Thr Leu Lys Ile Phe Arg
```

```
                65                  70                  75                  80
Lys Gly Glu Leu Ala Gln Asp Tyr Asp Gly Pro Arg Val Ala Glu Gly
                    85                  90                  95
Ile Val Lys Tyr Met Arg Gly Gln Ala Gly Pro Ser Ala Thr Glu Ile
                100                 105                 110
Asn Thr Gln Gln Glu Phe Glu Lys Met Leu Gln Ala Asp Asp Val Thr
                115                 120                 125
Ile Cys Gly Phe Phe Glu Glu Asn Ser Lys Leu Lys Asp Ser Phe Leu
                130                 135                 140
Lys Val Ala Asp Thr Glu Arg Asp Arg Phe Lys Phe Val Trp Thr Ser
145                 150                 155                 160
Asn Lys Gln Ile Leu Glu Ser Arg Gly Tyr Asn Asp Asp Ile Val Ala
                165                 170                 175
Tyr Gln Pro Lys Lys Phe His Asn Lys Phe Glu Pro Asn Glu Phe Lys
                180                 185                 190
Tyr Asp Gly Asn Tyr Asp Thr Asp Lys Ile Lys Glu Phe Leu Leu His
                195                 200                 205
Glu Thr Asn Gly Leu Val Gly Ile Arg Thr Ala Glu Asn Arg Tyr Gln
                210                 215                 220
Tyr Asp Leu Leu Pro Met Phe Val Val Tyr Gly
225                 230                 235
```

(2) INFORMATION FOR SEQ ID NO:7:

(i) SEQUENCE CHARACTERISTICS:
        (A) LENGTH: 707 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TTGCCATAGA CGACGAACAT CGGAAGTAGA TCATACTGAT AACGGTTTTC GGCCGTTCGT    60
ATACCAACAA GCCCATTTGT TTCGTGTAGG AGAAATTCTT TAATCTTGTC TGTGTCGTAA   120
TTTCCATCAT ACTTGAATTC ATTTGGTTCA AATTTATTAT GAAATTTCTT CGGTTGATAT   180
GCGACGATAT CATCATTGTA TCCCCTTGAT TCCAGAATTT GTTTATTTGA TGTCCACACA   240
AACTTAAAAC GATCTCTTTC TGTATCCGCA ACTTTTAAGA ATGAGTCTTT TAACTTGCTG   300
TTCTCTTCGA AAAATCCACA AATAGTAACG TCATCGGCTT GCAACATTTT TTCGAATTCT   360
TGTTGTGTAT TAATTTCTGT AGCTGATGGA CCTGCCTGTC CACGCATATA TTTCACAATA   420
CCTTCTGCTA CTCTCGGACC ATCATAATCC TGTGCTAGTT CTCCCTTACG GAAAATTTTC   480
AAAGTCGGGA AGCCACTAAC ACCGTATTCA TCGCAAGTTT TCTTCTCCTC CGTACAGTCA   540
ACCTCTGCTA AATGAATAGG CGGATCATTC TGTAAAAGTT TGGTTGCTGC TTTTTCAAAT   600
TCTGGTGCTA TCTTTTTGCA GTGTCCGCAC CATGGTGCAT AAAATTTCAC AAGTAATACA   660
TCATATGGTT TAATTCCCTC CTTGAAGTCC GCATCTGTAA ATTTCAT              707
```

(2) INFORMATION FOR SEQ ID NO:8:

(i) SEQUENCE CHARACTERISTICS:
        (A) LENGTH: 705 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
ATGAAATTTA CAGATGCGGA CTTCAAGGAG GGAATTAAAC CATATGATGT ATTACTTGTG    60
AAATTTTATG CACCATGGTG CGGACACTGC AAAAAGATAG CACCAGAATT TGAAAAAGCA   120
GCAACCAAAC TTTTACAGAA TGATCCGCCT ATTCATTTAG CAGAGGTTGA CTGTACGGAG   180
GAGAAGAAAA CTTGCGATGA ATACGGTGTT AGTGGCTTCC CGACTTTGAA AATTTTCCGT   240
AAGGGAGAAC TAGCACAGGA TTATGATGGT CCGAGAGTAG CAGAAGGTAT TGTGAAATAT   300
ATGCGTGGAC AGGCAGGTCC ATCAGCTACA GAAATTAATA CACAACAAGA ATTCGAAAAA   360
ATGTTGCAAG CCGATGACGT TACTATTTGT GGATTTTTCG AAGAGAACAG CAAGTTAAAA   420
GACTCATTCT TAAAAGTTGC GGATACAGAA AGAGATCGTT TTAAGTTTGT GTGGACATCA   480
AATAAACAAA TTCTGGAATC AAGGGGATAC AATGATGATA TCGTCGCATA TCAACCGAAG   540
AAATTTCATA ATAAATTTGA ACCAAATGAA TTCAAGTATG ATGGAAATTA CGACACAGAC   600
AAGATTAAAG AATTTCTCCT ACACGAAACA AATGGGCTTG TTGGTATACG AACGGCCGAA   660
AACCGTTATC AGTATGATCT ACTTCCGATG TTCGTCGTCT ATGGC              705
```

(2) INFORMATION FOR SEQ ID NO:9:

(i) SEQUENCE CHARACTERISTICS:
        (A) LENGTH: 705 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GCCATAGACG ACGAACATCG GAAGTAGATC ATACTGATAA CGGTTTTCGG CCGTTCGTAT    60
ACCAACAAGC CCATTTGTTT CGTGTAGGAG AAATTCTTTA ATCTTGTCTG TGTCGTAATT   120
TCCATCATAC TTGAATTCAT TTGGTTCAAA TTTATTATGA AATTTCTTCG GTTGATATGC   180
GACGATATCA TCATTGTATC CCCTTGATTC CAGAATTTGT TTATTTGATG TCCACACAAA   240
CTTAAAACGA TCTCTTTCTG TATCCGCAAC TTTTAAGAAT GAGTCTTTTA ACTTGCTGTT   300
CTCTTCGAAA AATCCACAAA TAGTAACGTC ATCGGCTTGC AACATTTTTT CGAATTCTTG   360
TTGTGTATTA ATTTCTGTAG CTGATGGACC TGCCTGTCCA CGCATATATT TCACAATACC   420
TTCTGCTACT CTCGGACCAT CATAATCCTG TGCTAGTTCT CCCTTACGGA AAATTTTCAA   480
AGTCGGGAAG CCACTAACAC CGTATTCATC GCAAGTTTTC TTCTCCTCCG TACAGTCAAC   540
CTCTGCTAAA TGAATAGGCG GATCATTCTG TAAAAGTTTG GTTGCTGCTT TTTCAAATTC   600
TGGTGCTATC TTTTTGCAGT GTCCGCACCA TGGTGCATAA AATTTCACAA GTAATACATC   660
ATATGGTTTA ATTCCCTCCT TGAAGTCCGC ATCTGTAAAT TTCAT              705
```

(2) INFORMATION FOR SEQ ID NO:10:

(i) SEQUENCE CHARACTERISTICS:
        (A) LENGTH: 1472 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1105

(xi) SEQUENCE DESCRIPTION: SEQ ID NO:10:

| | | | | | | | | | | | | | | | | |
|---|---|---|---|---|---|---|---|---|---|---|---|---|---|---|---|---|
| T | ATG | CGT | GGA | CAG | GCA | GGT | CCA | TCA | GCT | ACA | GAA | ATT | AAT | ACA | CAA | CAA | 49 |
| | Met | Arg | Gly | Gln | Ala | Gly | Pro | Ser | Ala | Thr | Glu | Ile | Asn | Thr | Gln | Gln |
| | 1 | | | 5 | | | | | 10 | | | | | 15 |

| GAA | TTC | GAA | AAA | ATG | TTG | CAA | GCC | GAT | GAC | GTT | ACT | ATT | TGT | GGA | TTT | 97 |
|---|---|---|---|---|---|---|---|---|---|---|---|---|---|---|---|---|
| Glu | Phe | Glu | Lys | Met | Leu | Gln | Ala | Asp | Asp | Val | Thr | Ile | Cys | Gly | Phe |
| | | | 20 | | | | | 25 | | | | | 30 |

| TTC | GAA | GAG | AAC | AGC | AAG | TTA | AAA | GAC | TCA | TTC | TTA | AAA | GTT | GCG | GAT | 145 |
|---|---|---|---|---|---|---|---|---|---|---|---|---|---|---|---|---|
| Phe | Glu | Glu | Asn | Ser | Lys | Leu | Lys | Asp | Ser | Phe | Leu | Lys | Val | Ala | Asp |
| | | 35 | | | | | 40 | | | | | 45 |

| ACA | GAA | AGA | GAT | CGT | TTT | AAG | TTT | GTG | TGG | ACA | TCA | AAT | AAA | CAA | ATT | 193 |
|---|---|---|---|---|---|---|---|---|---|---|---|---|---|---|---|---|
| Thr | Glu | Arg | Asp | Arg | Phe | Lys | Phe | Val | Trp | Thr | Ser | Asn | Lys | Gln | Ile |
| 50 | | | | | 55 | | | | | 60 |

| CTG | GAA | TCA | AGG | GGA | TAC | AAT | GAT | GAT | ATC | GTC | GCA | TAT | CAA | CCG | AAG | 241 |
|---|---|---|---|---|---|---|---|---|---|---|---|---|---|---|---|---|
| Leu | Glu | Ser | Arg | Gly | Tyr | Asn | Asp | Asp | Ile | Val | Ala | Tyr | Gln | Pro | Lys |
| 65 | | | | 70 | | | | | 75 | | | | | 80 |

| AAA | TTT | CAT | AAT | AAA | TTT | GAA | CCA | AAT | GAA | TTC | AAG | TAT | GAT | GGA | AAT | 289 |
|---|---|---|---|---|---|---|---|---|---|---|---|---|---|---|---|---|
| Lys | Phe | His | Asn | Lys | Phe | Glu | Pro | Asn | Glu | Phe | Lys | Tyr | Asp | Gly | Asn |
| | | | | 85 | | | | | 90 | | | | | 95 |

| TAC | GAC | ACA | GAC | AAG | ATT | AAA | GAA | TTT | CTC | CTA | CAC | GAA | ACA | AAT | GGG | 337 |
|---|---|---|---|---|---|---|---|---|---|---|---|---|---|---|---|---|
| Tyr | Asp | Thr | Asp | Lys | Ile | Lys | Glu | Phe | Leu | Leu | His | Glu | Thr | Asn | Gly |
| | | | 100 | | | | | 105 | | | | | 110 |

| CTT | GTT | GGT | ATA | CGA | ACG | GCC | GAA | AAC | CGT | TAT | CAG | TAT | GAT | CTA | CTT | 385 |
|---|---|---|---|---|---|---|---|---|---|---|---|---|---|---|---|---|
| Leu | Val | Gly | Ile | Arg | Thr | Ala | Glu | Asn | Arg | Tyr | Gln | Tyr | Asp | Leu | Leu |
| | | | 115 | | | | | 120 | | | | | 125 |

| CCG | ATG | TTT | GTT | GTG | TAT | GGC | AAG | GTT | GAC | TAT | GAA | TTG | GAT | CCA | AAA | 433 |
|---|---|---|---|---|---|---|---|---|---|---|---|---|---|---|---|---|
| Pro | Met | Phe | Val | Val | Tyr | Gly | Lys | Val | Asp | Tyr | Glu | Leu | Asp | Pro | Lys |
| | 130 | | | | | 135 | | | | | 140 |

| GGT | TCC | AAC | TAT | TGG | CGA | AAT | CGT | GTT | CTT | ATG | GTT | GCA | AAA | GAT | TAC | 481 |
|---|---|---|---|---|---|---|---|---|---|---|---|---|---|---|---|---|
| Gly | Ser | Asn | Tyr | Trp | Arg | Asn | Arg | Val | Leu | Met | Val | Ala | Lys | Asp | Tyr |
| 145 | | | | | 150 | | | | | 155 | | | | | 160 |

| AAA | AGG | AAA | GCA | AAT | TTT | GCT | ATG | AGT | AAC | AAA | GAA | GAC | TTC | TCT | TTT | 529 |
|---|---|---|---|---|---|---|---|---|---|---|---|---|---|---|---|---|
| Lys | Arg | Lys | Ala | Asn | Phe | Ala | Met | Ser | Asn | Lys | Glu | Asp | Phe | Ser | Phe |
| | | | | 165 | | | | | 170 | | | | | 175 |

| GAT | CTT | GAT | GAA | TTT | GGC | TTA | GCT | AAT | CGT | AAA | GAT | ACC | AAG | CCG | CTT | 577 |
|---|---|---|---|---|---|---|---|---|---|---|---|---|---|---|---|---|
| Asp | Leu | Asp | Glu | Phe | Gly | Leu | Ala | Asn | Arg | Lys | Asp | Thr | Lys | Pro | Leu |
| | | | 180 | | | | | 185 | | | | | 190 |

| GTT | GCA | GCA | CGT | AGC | AAA | AAA | GGC | AAA | TTC | TTT | ATG | AAA | GAA | GAA | TTC | 625 |
|---|---|---|---|---|---|---|---|---|---|---|---|---|---|---|---|---|
| Val | Ala | Ala | Arg | Ser | Lys | Lys | Gly | Lys | Phe | Phe | Met | Lys | Glu | Glu | Phe |
| | | | 195 | | | | | 200 | | | | | 205 |

| AGT | TTT | AGC | GTG | GAA | AAT | TTG | AAA | AAA | TTT | GTC | GAA | GAT | GTT | ATT | GGT | 673 |
|---|---|---|---|---|---|---|---|---|---|---|---|---|---|---|---|---|
| Ser | Phe | Ser | Val | Glu | Asn | Leu | Lys | Lys | Phe | Val | Glu | Asp | Val | Ile | Gly |
| | 210 | | | | | 215 | | | | | 220 |

| GAT | AGA | TTA | GAA | CCG | TAT | ATG | AAG | AGC | GAA | GAA | GCA | CCT | GAA | GAT | CAG | 721 |
|---|---|---|---|---|---|---|---|---|---|---|---|---|---|---|---|---|
| Asp | Arg | Leu | Glu | Pro | Tyr | Met | Lys | Ser | Glu | Glu | Ala | Pro | Glu | Asp | Gln |
| 225 | | | | | 230 | | | | | 235 | | | | | 240 |

| GGT | GAT | GTT | AAG | GTC | GTT | GTT | GCT | AAG | ACA | TTC | CAA | GAA | ATG | ATC | ATG | 769 |
|---|---|---|---|---|---|---|---|---|---|---|---|---|---|---|---|---|
| Gly | Asp | Val | Lys | Val | Val | Val | Ala | Lys | Thr | Phe | Gln | Glu | Met | Ile | Met |
| | | | | 245 | | | | | 250 | | | | | 255 |

| AAT | GTG | GAA | AAG | GAT | GTT | TTA | ATC | GAA | TTT | TAT | GCT | CCA | TGG | TGT | GGC | 817 |
|---|---|---|---|---|---|---|---|---|---|---|---|---|---|---|---|---|
| Asn | Val | Glu | Lys | Asp | Val | Leu | Ile | Glu | Phe | Tyr | Ala | Pro | Trp | Cys | Gly |
| | | | 260 | | | | | 265 | | | | | 270 |

| CAC | TGC | AAA | GCA | CTC | GCA | CCG | AAA | TAT | GAT | GAA | TTA | GGC | CAG | AAA | TTA | 865 |
|---|---|---|---|---|---|---|---|---|---|---|---|---|---|---|---|---|
| His | Cys | Lys | Ala | Leu | Ala | Pro | Lys | Tyr | Asp | Glu | Leu | Gly | Gln | Lys | Leu |
| | | 275 | | | | | 280 | | | | | 285 |

| TCC | GGT | GAA | CCA | GGT | GTT | GTT | ATT | GCA | AAA | ATG | GAC | GCA | ACA | GCG | AAT | 913 |
|---|---|---|---|---|---|---|---|---|---|---|---|---|---|---|---|---|
| Ser | Gly | Glu | Pro | Gly | Val | Val | Ile | Ala | Lys | Met | Asp | Ala | Thr | Ala | Asn |
| | 290 | | | | | 295 | | | | | 300 |

| GAT | GTC | CCA | CCA | CCA | TTC | CAA | GTA | CAA | GGA | TTT | CCA | ACT | CTT | TAC | TGG | 961 |

```
Asp Val Pro Pro Pro Phe Gln Val Gln Gly Phe Pro Thr Leu Tyr Trp
305                 310                 315                 320

GTA CCG AAG AAT AAA AAA GAC AAA CCA GAG CCA TAC TCT GGT GGT CGA    1009
Val Pro Lys Asn Lys Lys Asp Lys Pro Glu Pro Tyr Ser Gly Gly Arg
                325                 330                 335

GAA GTG GAT GAT TTT ATT AAA TAC ATC GCG AAG CAT GCA ACG GAA GAA    1057
Glu Val Asp Asp Phe Ile Lys Tyr Ile Ala Lys His Ala Thr Glu Glu
                340                 345                 350

CTG AAG GGA TAC AAG AGA GAT GGA AAA CCG AAG AAG AAG GAA GAA TTG    1105
Leu Lys Gly Tyr Lys Arg Asp Gly Lys Pro Lys Lys Lys Glu Glu Leu
                355                 360                 365

TAAAGGGTAA TAATGATGAA TTTTTAATTT GATGTGAACC CAAACAACCT CAGTTGCTTA   1165

TTGGTGGATA AATATTTAAA TCATTCCACA GAGCTGTGAT ATGAATTTTC AAATATGTTT   1225

TTTTTTGGTT TATTTGATA AATTCATATT TTAAGTTGTT ATTTTTTAGT GCCTTAGGCT    1285

GTTTCATCAG TTGCCTTAGG CTATTTTGTC AGTTCGGAAT GTTTATTCCG TTAGCTTAGG   1345

CTTTTTTTTG TTTACCTTAT GTTACTGTTG TTATTGTATT ACTATTTTGC CCTTGTTTTT   1405

TAAATTTTAA ATAAATTTTT TTTGGAAAAA AAAAAAAAAA AAAAAAAAAA AAAAAAAAAA   1465

AAAAAAA                                                            1472
```

(2) INFORMATION FOR SEQ ID NO:11:

(i) SEQUENCE CHARACTERISTICS:
       (A) LENGTH: 368 amino acids
       (B) TYPE: amino acid
       (D) TOPOLOGY: linear (ii) MOLECULE TYPE: protein (xi) SEQUENCE DESCRIPTION: SEQ ID NO:11:

```
Met Arg Gly Gln Ala Gly Pro Ser Ala Thr Glu Ile Asn Thr Gln Gln
 1               5                  10                  15

Glu Phe Glu Lys Met Leu Gln Ala Asp Asp Val Thr Ile Cys Gly Phe
                20                  25                  30

Phe Glu Glu Asn Ser Lys Leu Lys Asp Ser Phe Leu Lys Val Ala Asp
            35                  40                  45

Thr Glu Arg Asp Arg Phe Lys Phe Val Trp Thr Ser Asn Lys Gln Ile
 50                  55                  60

Leu Glu Ser Arg Gly Tyr Asn Asp Asp Ile Val Ala Tyr Gln Pro Lys
 65                  70                  75                  80

Lys Phe His Asn Lys Phe Glu Pro Asn Glu Phe Lys Tyr Asp Gly Asn
                85                  90                  95

Tyr Asp Thr Asp Lys Ile Lys Glu Phe Leu Leu His Glu Thr Asn Gly
            100                 105                 110

Leu Val Gly Ile Arg Thr Ala Glu Asn Arg Tyr Gln Tyr Asp Leu Leu
        115                 120                 125

Pro Met Phe Val Val Tyr Gly Lys Val Asp Tyr Glu Leu Asp Pro Lys
130                 135                 140

Gly Ser Asn Tyr Trp Arg Asn Arg Val Leu Met Val Ala Lys Asp Tyr
145                 150                 155                 160

Lys Arg Lys Ala Asn Phe Ala Met Ser Asn Lys Glu Asp Phe Ser Phe
                165                 170                 175

Asp Leu Asp Glu Phe Gly Leu Ala Asn Arg Lys Asp Thr Lys Pro Leu
            180                 185                 190

Val Ala Ala Arg Ser Lys Lys Gly Lys Phe Phe Met Lys Glu Glu Phe
        195                 200                 205
```

```
Ser Phe Ser Val Glu Asn Leu Lys Lys Phe Val Glu Asp Val Ile Gly
    210                 215                 220
Asp Arg Leu Glu Pro Tyr Met Lys Ser Glu Glu Ala Pro Glu Asp Gln
225                 230                 235                 240
Gly Asp Val Lys Val Val Ala Lys Thr Phe Gln Glu Met Ile Met
                245                 250                 255
Asn Val Glu Lys Asp Val Leu Ile Glu Phe Tyr Ala Pro Trp Cys Gly
                260                 265                 270
His Cys Lys Ala Leu Ala Pro Tyr Asp Glu Leu Gly Gln Lys Leu
            275                 280                 285
Ser Gly Glu Pro Gly Val Ile Ala Lys Met Asp Ala Thr Ala Asn
    290                 295                 300
Asp Val Pro Pro Pro Phe Gln Val Gln Gly Phe Pro Thr Leu Tyr Trp
305                 310                 315                 320
Val Pro Lys Asn Lys Asp Lys Pro Glu Pro Tyr Ser Gly Gly Arg
                325                 330                 335
Glu Val Asp Asp Phe Ile Lys Tyr Ile Ala Lys His Ala Thr Glu Glu
                340                 345                 350
Leu Lys Gly Tyr Lys Arg Asp Gly Lys Pro Lys Lys Glu Glu Leu
            355                 360                 365
```

(2) INFORMATION FOR SEQ ID NO:12:

(i) SEQUENCE CHARACTERISTICS:
        (A) LENGTH: 1472 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
TTTTTTTTTT TTTTTTTTTT TTTTTTTTTT TTTTTTTTTT TTCCAAAAAA AATTTATTTA    60
AAATTTAAAA AACAAGGGCA AAATAGTAAT ACAATAACAA CAGTAACATA AGGTAAACAA   120
AAAAAAGCCT AAGCTAACGG AATAAACATT CCGAACTGAC AAAATAGCCT AAGGCAACTG   180
ATGAAACAGC CTAAGGCACT AAAAAATAAC AACTTAAAAT ATGAATTTAT CAAAATAAAC   240
CAAAAAAAAA CATATTTGAA AATTCATATC ACAGCTCTGT GGAATGATTT AAATATTTAT   300
CCACCAATAA GCAACTGAGG TTGTTTGGGT TCACATCAAA TTAAAAATTC ATCATTATTA   360
CCCTTTACAA TTCTTCCTTC TTCTTCGGTT TTCCATCTCT CTTGTATCCC TTCAGTTCTT   420
CCGTTGCATG CTTCGCGATG TATTTAATAA AATCATCCAC TTCTCGACCA CCAGAGTATG   480
GCTCTGGTTT GTCTTTTTTA TTCTTCGGTA CCCAGTAAAG AGTTGGAAAT CCTTGTACTT   540
GGAATGGTGG TGGGACATCA TTCGCTGTTG CGTCCATTTT TGCAATAACA AAACCTGGTT   600
CACCGGATAA TTTCTGGCCT AATTCATCAT ATTTCGGTGC GAGTGCTTTG CAGTGGCCAC   660
ACCATGGAGC ATAAAATTCG ATTAAAACAT CCTTTTCCAC ATTCATGATC ATTTCTTGGA   720
ATGTCTTAGC AACAACGACC TTAACATCAC CCTGATCTTC AGGTGCTTCT TCGCTCTTCA   780
TATACGGTTC TAATCTATCA CCAATAACAT CTTCGACAAA TTTTTTCAAA TTTTCCACGC   840
TAAAACTGAA TTCTTCTTTC ATAAAGAATT TGCCTTTTTT GCTACGTGCT GCAACAAGCG   900
GCTTGGTATC TTTACGATTA GCTAAGCCAA ATTCATCAAG ATCAAAAGAG AAGTCTTCTT   960
TGTTACTCAT AGCAAAATTT GCTTTCCTTT TGTAATCTTT TGCAACCATA AGAACACGAT  1020
TTCGCCAATA GTTGGAACCT TTTGGATCCA ATTCATAGTC AACCTTGCCA TACACAACAA  1080
```

| ACATCGGAAG TAGATCATAC TGATAACGGT TTTCGGCCGT TCGTATACCA ACAAGCCCAT | 1140 |
| TTGTTTCGTG TAGGAGAAAT TCTTTAATCT TGTCTGTGTC GTAATTTCCA TCATACTTGA | 1200 |
| ATTCATTTGG TTCAAATTTA TTATGAAATT TCTTCGGTTG ATATGCGACG ATATCATCAT | 1260 |
| TGTATCCCCT TGATTCCAGA ATTTGTTTAT TTGATGTCCA CACAAACTTA AAACGATCTC | 1320 |
| TTTCTGTATC CGCAACTTTT AAGAATGAGT CTTTTAACTT GCTGTTCTCT TCGAAAAATC | 1380 |
| CACAAATAGT AACGTCATCG GCTTGCAACA TTTTTTCGAA TTCTTGTTGT GTATTAATTT | 1440 |
| CTGTAGCTGA TGGACCTGCC TGTCCACGCA TA | 1472 |

(2) INFORMATION FOR SEQ ID NO:13:

(i) SEQUENCE CHARACTERISTICS:
        (A) LENGTH: 1107 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

| ATGCGTGGAC AGGCAGGTCC ATCAGCTACA GAAATTAATA CACAACAAGA ATTCGAAAAA | 60 |
| ATGTTGCAAG CCGATGACGT TACTATTTGT GGATTTTTCG AAGAGAACAG CAAGTTAAAA | 120 |
| GACTCATTCT TAAAAGTTGC GGATACAGAA AGAGATCGTT TTAAGTTTGT GTGGACATCA | 180 |
| AATAAACAAA TTCTGGAATC AAGGGGATAC AATGATGATA TCGTCGCATA TCAACCGAAG | 240 |
| AAATTTCATA ATAAATTTGA ACCAAATGAA TTCAAGTATG ATGGAAATTA CGACACAGAC | 300 |
| AAGATTAAAG AATTTCTCCT ACACGAAACA ATGGGCTTG TTGGTATACG AACGGCCGAA | 360 |
| AACCGTTATC AGTATGATCT ACTTCCGATG TTTGTTGTGT ATGGCAAGGT TGACTATGAA | 420 |
| TTGGATCCAA AAGGTTCCAA CTATTGGCGA ATCGTGTTC TTATGGTTGC AAAAGATTAC | 480 |
| AAAAGGAAAG CAAATTTTGC TATGAGTAAC AAAGAAGACT TCTCTTTTGA TCTTGATGAA | 540 |
| TTTGGCTTAG CTAATCGTAA AGATACCAAG CCGCTTGTTG CAGCACGTAG CAAAAAAGGC | 600 |
| AAATTCTTTA TGAAAGAAGA ATTCAGTTTT AGCGTGGAAA ATTTGAAAAA ATTTGTCGAA | 660 |
| GATGTTATTG GTGATAGATT AGAACCGTAT ATGAAGAGCG AAGAAGCACC TGAAGATCAG | 720 |
| GGTGATGTTA AGGTCGTTGT TGCTAAGACA TTCCAAGAAA TGATCATGAA TGTGGAAAAG | 780 |
| GATGTTTTAA TCGAATTTTA TGCTCCATGG TGTGGCCACT GCAAAGCACT CGCACCGAAA | 840 |
| TATGATGAAT TAGGCCAGAA ATTATCCGGT GAACCAGGTG TTGTTATTGC AAAAATGGAC | 900 |
| GCAACAGCGA ATGATGTCCC ACCACCATTC AAGTACAAG GATTTCCAAC TCTTTACTGG | 960 |
| GTACCGAAGA ATAAAAAAGA CAAACCAGAG CCATACTCTG GTGGTCGAGA AGTGGATGAT | 1020 |
| TTTATTAAAT ACATCGCGAA GCATGCAACG GAAGAACTGA AGGGATACAA GAGAGATGGA | 1080 |
| AAACCGAAGA AGAAGGAAGA ATTGTAA | 1107 |

(2) INFORMATION FOR SEQ ID NO:14:

(i) SEQUENCE CHARACTERISTICS:
        (A) LENGTH: 1107 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
TTACAATTCT TCCTTCTTCT TCGGTTTTCC ATCTCTCTTG TATCCCTTCA GTTCTTCCGT     60

TGCATGCTTC GCGATGTATT TAATAAAATC ATCCACTTCT CGACCACCAG AGTATGGCTC    120

TGGTTTGTCT TTTTTATTCT TCGGTACCCA GTAAAGAGTT GGAAATCCTT GTACTTGGAA    180

TGGTGGTGGG ACATCATTCG CTGTTGCGTC CATTTTTGCA ATAACAACAC CTGGTTCACC    240

GGATAATTTC TGGCCTAATT CATCATATTT CGGTGCGAGT GCTTTGCAGT GGCCACACCA    300

TGGAGCATAA AATTCGATTA AACATCCTT  TTCCACATTC ATGATCATTT CTTGGAATGT    360

CTTAGCAACA ACGACCTTAA CATCACCCTG ATCTTCAGGT GCTTCTTCGC TCTTCATATA    420

CGGTTCTAAT CTATCACCAA TAACATCTTC GACAAATTTT TCAAATTTT  CCACGCTAAA    480

ACTGAATTCT TCTTTCATAA AGAATTTGCC TTTTTTGCTA CGTGCTGCAA CAAGCGGCTT    540

GGTATCTTTA CGATTAGCTA AGCCAAATTC ATCAAGATCA AAAGAGAAGT CTTCTTTGTT    600

ACTCATAGCA AAATTTGCTT TCCTTTTGTA ATCTTTTGCA ACCATAAGAA CACGATTTCG    660

CCAATAGTTG GAACCTTTTG GATCCAATTC ATAGTCAACC TTGCCATACA CAACAAACAT    720

CGGAAGTAGA TCATACTGAT AACGGTTTTC GGCCGTTCGT ATACCAACAA GCCCATTTGT    780

TTCGTGTAGG AGAAATTCTT TAATCTTGTC TGTGTCGTAA TTTCCATCAT ACTTGAATTC    840

ATTTGGTTCA AATTTATTAT GAAATTTCTT CGGTTGATAT GCGACGATAT CATCATTGTA    900

TCCCCTTGAT TCCAGAATTT GTTTATTTGA TGTCCACACA AACTTAAAAC GATCTCTTTC    960

TGTATCCGCA ACTTTTAAGA ATGAGTCTTT TAACTTGCTG TTCTCTTCGA AAAATCCACA   1020

AATAGTAACG TCATCGGCTT GCAACATTTT TTCGAATTCT TGTTGTGTAT TAATTTCTGT   1080

AGCTGATGGA CCTGCCTGTC CACGCAT                                      1107

(2) INFORMATION FOR SEQ ID NO:15:

(i) SEQUENCE CHARACTERISTICS:
        (A) LENGTH:  32
        (B) TYPE:  nucleic acid
        (C) STRANDEDNESS:  single
        (D) TOPOLOGY:  linear (ii) MOLECULE TYPE:  primer (xi) SEQUENCE DESCRIPTION: SEQ ID NO:15:

ATGAARTTYA CNGAYGCNGA YTTYAARGAR GG                                  32

(2) INFORMATION FOR SEQ ID NO:16:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  primer (xi) SEQUENCE DESCRIPTION: SEQ ID NO:16:

TTNCCRTANA CNACRAACAT                                                20

(2) INFORMATION FOR SEQ ID NO:17:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  primer
```

-continued (xi) SEQUENCE DESCRIPTION: SEQ ID NO:17:

AATTAACCCT CACTAAAGGG                                                    20

(2) INFORMATION FOR SEQ ID NO:18:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:18:

GTAATACGAC TCACTATAGG GC                                                 22

(2) INFORMATION FOR SEQ ID NO:19:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:19:

GAAAACCGTT ATCAGTATGA TCT                                                23

(2) INFORMATION FOR SEQ ID NO:20:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:20:

CTGTGGAATG ATTTAAATAT TTATCC                                             26

(2) INFORMATION FOR SEQ ID NO:21:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:21:

GTCCATTTTT GCAATAACAA CACC                                               24

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molcule selected from the group consisting of: (a) a *Dirofilaria immitis* nucleic acid molecule comprising a nucleic acid sequence selected from the group consisting of SEQ ID NO:5, SEQ ID NO:7, SEQ ID NO:8, SEQ ID NO:9, SEQ ID NO:10, SEQ ID NO:12, SEQ ID NO:13 and SEQ ID NO:14; (b) a *Dirofilaria immitis* nucleic acid molecule conprising a nucleic acid homologue of a nucleic acid molecule comprising a nuclcic acid sequence selectcd from the group consisting of SEQ ID NO:5, SEQ ID NO:8, SEQ ID NO:10, and SEQ ID NO:13, wherein said homologue comprises at least 18 contiguous nucleotides of any one of said nucleic acid sequences rcited in (b), which said homologue encodes a protein containing one or more amino acid deletions, substitutions, or insertions as compared to a protein encoded by a nucleic acid molecule having a nucleic acid sequence as recited in (b), and wherein said protein comprises at least one epitope that elicits an immune response against a protein having an amino acid sequence selected from the group consisting of SEQ ID NO:6 and SEQ ID NO:11: and (c) a *Dirofilaria immitis* nucleic acid molecule which is fully complementary to any said nucleic acid molecule recited in (b).

2. The nucleic acid molocule of claim 1, wherein said nucleic acid molecule comprises a nucleic acid sequence selected from the group consisting of SEQ ID NO:5, SEQ ID NO:7, SEQ ID NO:8, SEQ ID NO:9, SEQ ID NO:10, SEQ ID NO:12, SEQ ID NO:13 and SEQ ID NO:14.

3. The nucleic acid molecule of claim 1, wherein said nucleic acid molecule comprises an oligonucleotide.

4. A recombinant molecule comprising a nucleic acid molecule as set forth in claim 1 operatively linked to a transcription control sequence.

5. A recombinant virus comprising a nucleic acid molecule as set forth in claim 1.

6. A recombinant cell comprising a nucleic acid molecule as set forth in claim 1.

7. An isolated nucleic acid molecule selected from the group consisting of: (a) an isolated *Dirofilaria immitis* nucleic acid molecule comprising a nucleic acid sequence encoding a protein selected from the group consisting of (i) a protein having an amino acid sequence selected from the group consisting of SEQ ID NO:6, and SEQ ID NO:11, and (ii) a protein comprising a homologue of a protein having an amino acid sequence selected from the group consisting of SEQ ID NO:6, and SEQ ID NO:11, wherein said homologue comprises at least 6 contiguous amino acids of any one of said amino acid sequences, wherein said homologue encodes a protein containing one or more amino acid deletions, substitutions, or insertions, and wherein said protein comprises at least one epitope that elicits an immune response against a protein having an amino acid sequence selected from the group consisting of SEQ ID NO:6 and SEQ ID NO:11; and (b) an isolated *Dirofilaria immitis* nucleic acid molecule which is fully complementary to any said nucleic acid molecule recited in (a).

8. The nucleic acid molecule of claim 7, wherein said nucleic acid molecule encodes a protein having an amino acid sequence selected from the group consisting of, SEQ ID NO:6 and SEQ ID NO:11.

9. A method to produce a parasitic nematode transglutaminase protein, said method comprising culturing a cell transformed with a nucleic acid molecule comprising an isolated *Dirofilaria immitis* nucleic acid molecule comprising a nucleic acid sequence encoding a protein selected from the group consisting of a protein having an amino acid sequence selected from the group consisting of (i) SEQ ID NO:6, and SEQ ID NO:11, and (ii) a protein comprising a homologue of a protein having an amino acid sequence selected from the group consisting of SEQ ID NO:6, and SEQ ID NO:11, wherein said homologue comprises at least 6 contiguous amino acids of any one of said amino acid sequences, wherein said homologue encodes a protein containing one or more amino acid deletions, substitutions, or insertions, and wherein said protein comprises at least one epitope that elicits an immune response against a protein having an amino acid sequence selected from the group consisting of SEQ ID NO:6 and SEQ ID NO:11.

10. The method of claim 1, wherein said cell comprises a nucleic acid molecule comprising a nucleic acid sequence selected from the group consisting of SEQ ID NO:5, SEQ ID NO:8, SEQ ID NO:10, and SEQ ID NO:13.

\* \* \* \* \*

UNITED STATES PATENT AND TRADEMARK OFFICE
CERTIFICATE OF CORRECTION

PATENT NO. : 6,248,872 B1
DATED : June 19, 2001
INVENTOR(S) : Ramaswamy Chandrashekar It is certified that error appears in the above-identified patent and that said Letters Patent is hereby corrected as shown below:

Title page,
Item [54], please delete "TRANSGLUTAMINASE, NUCLEIC ACID" and replace with -- TRANSGLUTAMINASE NUCLEIC ACID --.

Item [56], OTHER PUBLICATIONS, please delete "Mierendorg" and replace with -- Mierendorf --.

Column 60,
Line 62, please delete "rcited" and replace with -- recited --.

Column 61,
Line 6, please delete "molocule" and replace with -- molecule --.

Signed and Sealed this

Twenty-second Day of April, 2003

JAMES E. ROGAN
*Director of the United States Patent and Trademark Office*